US008036915B2

(12) United States Patent
Kremer et al.

(10) Patent No.: US 8,036,915 B2
(45) Date of Patent: Oct. 11, 2011

(54) SYSTEM AND METHOD FOR COLLECTING AND MANAGING PATIENT DATA

(75) Inventors: Joel Kremer, Albany, NY (US); Timothy Harrington, Madison, WI (US); George Reed, Worcester, MA (US); Allan Gibofsky, New York, NY (US); Jeffrey Greenberg, Milburn, NJ (US)

(73) Assignee: Cosortium of Rheumatology Researchers of North America, Inc., Fonda, NY (US)

( * ) Notice: Subject to any disclaimer, the term of this patent is extended or adjusted under 35 U.S.C. 154(b) by 0 days.

(21) Appl. No.: 12/533,476

(22) Filed: Jul. 31, 2009

(65) Prior Publication Data

US 2010/0063848 A1    Mar. 11, 2010

Related U.S. Application Data

(60) Provisional application No. 61/085,095, filed on Jul. 31, 2008.

(51) Int. Cl.
 G06Q 10/00 (2006.01)
 G06Q 50/00 (2006.01)
(52) U.S. Cl. ................................................. 705/2; 705/3
(58) Field of Classification Search .................. 705/2–3; 600/300
See application file for complete search history.

(56) References Cited

U.S. PATENT DOCUMENTS

| 7,353,238 | B1 | 4/2008 | Gliklich |
| 2003/0046114 | A1 | 3/2003 | Davies et al. |
| 2003/0208454 | A1 | 11/2003 | Rienhoff, Jr. et al. |
| 2007/0106536 | A1 | 5/2007 | Moore |
| 2008/0059250 | A1* | 3/2008 | Joao ................................... 705/3 |
| 2008/0097794 | A1 | 4/2008 | Arnaud et al. |

OTHER PUBLICATIONS

Weaver, "Reaching the Goal of Remission in Rheumatoid Arthritis", Coalition of Rheumatology Educators, vol. 1 No. 1 [online] Oct. 2007.
Corrona, Questionnaires version 1, Nov. 26, 2001, numbered 1-13.
Corrona, Questionnaires version 2, Jan. 24, 2002, numbered 1-13.
Corrona, Questionnaires version 3, Jul. 4, 2002, numbered 1-13.
Corrona, Questionnaires version 4, Apr. 8, 2003, numbered 1-11.
Corrona, Questionnaires version 5, Jan. 5, 2004, numbered 1-11.
Corrona, Questionnaires versions 6 and 6a, Jan. 1, 2006, numbered 1-24.

* cited by examiner

*Primary Examiner* — Luke Gilligan
(74) *Attorney, Agent, or Firm* — Drinker Biddle & Reath LLP

(57) ABSTRACT

A system and method that employs standardized data collection forms for use by health care providers and patients to enable efficient collection, storage and management of patient data for treatment of diseases, such as rheumatoid arthritis.

21 Claims, 43 Drawing Sheets

CORRONA Physician Review Enrollment

Page 1                                                                   Site ID ☐

Please complete the Patient ID information on every page of the questionnaire.

Patient ID ☐☐☐ - ☐☐ - ☐☐☐☐     Date of office visit (MM/DD/YY) ☐☐/☐☐/☐☐

Always Complete at least Sections A, B, C, I, and M.

A. Your CORRONA Physician ID number ☐☐ (2 digits)

B. CURRENT RHEUMATIC DIAGNOSIS(ES). Please complete all boxes and circles that apply.

Year of onset    Disease severity (fill one per Dx) 1=Mild → 5=Severe

☐ OA → ☐☐ → ○1 ○2 ○3 ○4 ○5   OA →   PATIENTS WITH OA: JOINTS AFFECTED
☐ Hip ☐ Knee ☐ Spine ☐ Hand ☐ Other

☐ OP → ☐☐ → ○1 ○2→○3 ○4 ○5

☐ OP risk → ☐☐ → ○1 ○2 ○3 ○4 ○5

PATIENTS WITH NEW ONSET, RA, or PA
Complete at each visit.
i. ACR Functional Class   ○I. ○II. ○III. ○IV.

☐ New onset Undiff. Arth. (Not yet RA or PsA) → Weeks since onset of signs or symptoms ☐☐   New → ii. 28-Joint Counts ☐☐ ☐☐   Tender   Swollen

☐ RA → ☐☐ → ○1 ○2 ○3 ○4 ○5   RA → iii. Subcutaneous nodules   ○No ○Yes iv. Clinical joint deformity (hands, wrists, feet)   ○No ○Yes ☐ Psoriatic Arthritis ☐☐ → ○1 ○2 ○3 ○4 ○5   PA →

Indicate Subtype: ☐ RA Like ☐ Asymm. Oligo. ☐ Spondylitis ☐ DIP

Complete box if blood has been obtained for genetic testing at this visit: ☐ Biomarkers ☐

Is patient enrolled in CORRONA Psoriatic Pilot Study? ○No ○Yes

Does patient now/ever meet ACR criteria for the diagnosis indicated? ○No ○Yes

C. PHYSICIAN GLOBAL ASSESSMENT OF CURRENT DISEASE ACTIVITY (refers to primary diagnosis)
Put a mark (like this | ) on the scale:
NOT ACTIVE · · · · · · · · · · · · · · · · · · · · · · · · · · · · · · · · · · · · · · · · VERY ACTIVE
0 5 10 15 20 25 30 35 40 45 50 55 60 65 70 75 80 85 90 95 100

FROM FIG. 3A

| "DISPATCHER" BOX | Complete all corresponding sections IF this patient has EVER had any of the following: |
|---|---|

FILL ONE CIRCLE FOR EACH LETTER: | No | Yes

- D. Hospitalization → ○ ○
- E. Infections → ○ ○
- F. Comorbidities, Drug Toxicities, Fractures → ○ ○
- G. Joint Surgery → ○ ○
- H. Joint Arthrocentesis → ○ ○
- I. Concomitant Medications / Drug Changes → ○ ○
- J. Radiographs, MRI, Ultrasound → ○ ○
- K. Bone Densitometry → ○ ○

D. HOSPITALIZATION Fill all boxes that apply.
☐ For RA, not related to joint arthroplasty, but for the disease process itself.
☐ For reasons other than RA disease process (specify):
☐ Drug-related toxicity (see sections E and F) ☐ Joint anthroplasty ☐ Unrelated medical problem Site ID _____   Copyright 2000-2008 © CORRONA, Inc.
2008-10-15 MD Bsl. v.7 Pg. 1 of 4    Page 1

FIG. 3B

CORRONA Physician Review Enrollment

Page 2            Site ID [ ]

Please complete the Patient ID information on every page of the questionnaire.

Patient ID [ ][ ][ ] - [ ][ ] - [ ][ ][ ][ ]    Date of office visit (MM/DD/YY) [ ][ ] / [ ][ ] / [ ][ ]

E. INFECTIONS Fill all boxes that apply and indicate Pathogen.

| # - Infection Site: | Year of onset | Path Code: | # - Infection Site: | Year of onset | Path Code: |
|---|---|---|---|---|---|
| 1 - ☐ Joint/Bursa | | | 7 - ☐ Bronchitis | | |
| 2 - ☐ Cellulitis | | | 8 - ☐ Other _____ | | |
| 3 - ☐ Sinusitis | | | | | |
| 4 - ☐ Diverticulitis | | | | | |
| 5 - ☐ Sepsis | | | | | |
| 6 - ☐ Pneumonia | | | | | |

Pathogen codes
CD = Coccidiodomycosis
CY = Cryptococcus
HA = H.zoster
HP = Histoplasmosis
LI = Listeria
NO = Non-opportunistic
OO = Other opportunistic
PN = Pneumocystis
TB = TB IF the patient was hospitalized, please enter the infection(s) Site number listed above. [ ]
IF the patient required IV antibiotics, please enter the Infection Site number listed above. [ ]
IF the hospitalization was attributable to specific drug use, please enter the drug code. [ ] (Refer to Section F codes.)

F. COMORBIDITIES, DRUG TOXICITIES, FRACTURES

If any of the following are present, fill the box under "Co-M/Tox" and write the 2-digit year of onset. If a drug toxicity, please select the most responsible drug code from the list below.

| Fill if Co-M/Tox | Drug Code | YY of onset | Fill if Co-M/Tox | Drug Code | YY of onset | Fill if Co-M/Tox | Drug Code | YY of onset |
|---|---|---|---|---|---|---|---|---|
| ☐ Hypertension | | | ☐ Ulcer (peptic/bleeding) | | | ☐ Psychiatric disease (other) | | |
| ☐ CAD (Stent, CABG, Cath) | | | ☐ GERD | | | ☐ Depression | | |
| ☐ MI | | | ☐ Dyspepsia | | | ☐ Pulmonary fibrosis | | |
| ☐ CHF | | | ☐ Elevated creatinine | | | ☐ Asthma | | |
| ☐ Unstable Angina | | | ☐ Diarrhea | | | ☐ COPD | | |
| ☐ Edema | | | ☐ Nausea | | | ☐ Low WBC | | |
| ☐ Stroke/Mini-stroke | | | ☐ Live disorder | | | ☐ Anemia | | |
| ☐ DVT | | | ☐ Drug-induced SLE | | | ☐ Diabetes mellitus | | |
| ☐ Lymphoma | | | ☐ Rash | | | ☐ Infusion reaction | | |
| ☐ Lung cancer | | | ☐ Psoriasis (not arthritis) | | | ↳ ○ Mild ○ Moderate ○ Severe | | |
| ☐ Breast cancer | | | ☐ Alopecia | | | ☐ Other | | |
| ☐ Cancer (skin) | | | ☐ Demyelinating illness | | | ☐ Alcohol abuse ○ Now ○ Ever | | |
| ☐ Cancer (other) | | | | | | ☐ IV drug use ○ Now ○ Ever | | |
| ↳ _____ | | | | | | ☐ Tobacco use ○ Now ○ Ever | | |

FROM FIG. 4A

| Were any of these toxicities reported to the FDA? ○ No  ○ Yes  If Yes, enter drug code: ___ |

DRUG CODES TO ENTER IN SECTIONS E and F:
51 Prednisone   60 Kineret    15 Remicade       21 Actonel    29 Fosamax         35 Celebrex
52 Arava        10 MTX        18 Rituxan         22 Aredia     32 Invest. OP Drug  40 Ibuprofen
56 Enbrel       17 Orencia    20 Invest. DMARD   24 Boniva     31 Other OP Drug    50 Invest. NSAID
58 Humira       99 Other drug 19 Other DMARD     23 Didronel   33 Reclast          41 Naproxen
                                                 28 Forteo                         39 Other NSAID Indicate the 2 most recent fractures                                                Enter year.
         Most recent:    □ Wrist □ Hip □ Spine □ Rib(s) □ Pelvis □ Other            Yr.
         Second most recent: □ Wrist □ Hip □ Spine □ Rib(s) □ Pelvis □ Other

G. JOINT SURGERY Related to RA/arthritis only. Fill all boxes that apply.       Yr. of
     Site: □ Hip      □ Knee      □ Hand/wrist □ Carpal tunnel □ Shoulder           most recent
           □ Elbow    □ Foot/ankle □ C Spine    □ Other

H. JOINT ARTHROCENTESIS Include all steroid injections into joints, tendons, and bursa.
    Do not include diagnostic aspirations.                                  How many steroid injections?
Fill all that apply: □ Synvisc □ Hyalgan □ Supartz □ Orthovisc □ Eufflexa □ Corticosteroid ○1 ○2 ○3 ○4+

Site ID [    ]     Copyright 2000-2008 © CORRONA, Inc.          Page 2
                   2007-10-15 MD Bsl. v.7 Pg. 2 of 4

FIG. 4B

CORRONA Physician Review Enrollment

Page 3  Site ID [ ]

Please complete the Patient ID information on every page of the questionnaire.

Patient ID [ ][ ][ ] - [ ][ ] - [ ][ ][ ][ ]   Date of office visit (MM/DD/YY) [ ][ ] / [ ][ ] / [ ][ ]

I. Prior biologic drug history

Requires start and stop dates.

| Drug | Date started (MM/YY) | Date stopped (MM/YY) | Reason code* |
|---|---|---|---|
| Enbrel | ___/___ | ___/___ | Reason code*___ |
| Humira | ___/___ | ___/___ | Reason code*___ |
| Kineret | ___/___ | ___/___ | Reason code*___ |
| Orencia | ___/___ | ___/___ | Reason code*___ |
| Remicade | ___/___ | ___/___ | Reason code*___ |
| Rituxan | ___/___ | ___/___ | Reason code*___ | i. Current biologics  Include any changes made today.

△ ○ □ Enbrel     ○ 25 mg once weekly   ○ 25 mg twice weekly   ○ 50 mg once weekly   ○ Other ____

△ ○ □ Humira    ○ 40 mg every 2 weekly  ○ 40 mg weekly   ○ Other ____

△ ○ □ Remicade  ○ Every 8 weeks  ○ Every 4 weeks  ○ Every 6 weeks  ○ Every ___ weeks  No. of vials: ___.___

△ ○ □ Orencia   ○ First Dose   ○ 2 weeks after first dose   ○ 2 weeks after second dose
               ○ Every 4 weeks     ○ 2 vials = 500 mg   ○ 3 vials = 750 mg   ○ 4 vials = 1 g △ ○ □ Rituxan   Date of last infusion ___/___/___      ○ 500 mg   ○ 1,000 mg   ○ Other _____

△ ○ □ Kineret   ○ 100 mg daily   ○ Other ____

△ ○ □ Other Biologic ii. Other current drug use. (Please include dose, change, reason code(s), and dates.)

Drugs starting today = △
Drugs continued today = ○
Drugs discontinued today = □

□ Patient is not taking any of these drugs.

Reason Codes
If initiating or discontinuing therapy.

A - Lack of efficacy
B - Toxicity *
C - No longer needed
D - Lymphoma/malignancy
F - Formulary restriction

| Drug | Dose (mg) | If Changed Today | Reason Code(s)* |
|---|---|---|---|
| △ ○ □ Prednisone / d | | ○ | |
| △ ○ □ Arava / d | | ○ | |
| △ ○ □ Azulfidine / d | | ○ | |
| △ ○ □ Enbrel → | | ○ | |
| △ ○ □ Humira → | | ○ | |
| △ ○ □ Imuran / d | | ○ | |
| △ ○ □ Kineret → | | ○ | |
| DMARD △ ○ □ MTX / wk | | ○ | |
| △ ○ □ Orencia → | | ○ | |
| △ ○ □ Plaquenil / d | | ○ | |

FROM FIG. 5A

| | | | |
|---|---|---|---|
| H - Patient preference | △ ○ ☐ Remicade → | ○ | |
| I - Control of disease | △ ○ ☐ Rituxan → | ○ | |
| J - Infection | △ ○ ☐ Other Biologic | ○ | |
| K - Lack of insurance | △ ○ ☐ Other DMARD | ○ | |
| M - Recent journal report | △ ○ ☐ Invest. DMARD → | ○ | |
| S - Recent meeting report | | | |
| V - Recent lecture | △ ○ ☐ Actonel / wk | ○ | |
| W - Withdrawn by FDA/Mfgr | △ ○ ☐ Aredia / 3 mo | ○ | |
| X - Physician preference | △ ○ ☐ Boniva / mo | | |
| Z - Peer suggestion | ↳ ☐ IV ☐ PO | | |

OP Drug:
- △ ○ ☐ Didronel / d
- △ ○ ☐ ERT/HRT / d
- △ ○ ☐ Evista / d
- △ ○ ☐ Forteo / d
- △ ○ ☐ Fosamax /wk
- △ ○ ☐ Miacalcin / d
- △ ○ ☐ Reclast / yr
- △ ○ ☐ Invest. OP Drug →
- △ ○ ☐ Other OP Drug

*\* If reason is toxicity, please enter specific toxicity and responsible drug code in Section F.*

Site ID [ ]

Copyright 2000-2008 © CORRONA, Inc.
2007-10-15 MD Bsl. v.7 Pg. 3 of 4

Page 3

FIG. 5B

CORRONA Physician Review Enrollment

Page 4                                                                 Site ID [    ]

Please complete the Patient ID information on every page of the questionnaire.

Patient ID [   ]-[  ]-[    ]    Date of office visit (MM/DD/YY) [  ]/[  ]/[  ]

J. RADIOGRAPHS, MRI, ULTRASOUND

☐ MRI   ☐ Ultrasound
___ Erosions not seen on x-ray
___ Other bone changes
___ Active synovitis Date of *most recent* MRI, Ultrasound or Radiograph (MM/YY)
[  ]/[  ]

Radiographs - RA and PA Patients: (each finding requires a response)

|  | None | Old* | New | Old & New |
|---|---|---|---|---|
| Erosions | ○ | ○ | ○ | ○ |
| Joint space narrowing | ○ | ○ | ○ | ○ |
| Deformity | ○ | ○ | ○ | ○ |

☐ No previous for comparison *
☐ Healed erosion(s)

K. BONE DENSITOMETRY

Date of *most recent* BMD: (MM/YY) [  ]/[  ]

L spine  $^{+}_{-}$○ [  ].[  ]  or ☐ Not available
BMD (g/cm²) [  ].[  ]
Hip*  $^{+}_{-}$○ [  ].[  ]  or ☐ Not available
BMD (g/cm²) [  ].[  ]

t-scores / BMD values

Distal radius  $^{+}_{-}$○ [  ].[  ]  or ☐ Not available
BMD (g/cm²) [  ].[  ]

* "Hip" refers to: ○ Femoral Neck  ○ Total Hip  ○ Unknown

L. PSORIATIC ARTHRITIS i. CASPAR Criteria (Check all that apply.)
   ○ Current Psoriasis  ○ History of Psoriasis  ○ 1st/2nd degree relative with Psoriasis  ○ Nail changes with psoriasis
   ○ Negative RF  ○ Dactylitis in the past  ○ X-rays with juxta-articular new bone formation ii. Physician Global Assessment of Skin .................................................. VERY
       CLEAR  0 5 10 15 20 25 30 35 40 45 50 55 60 65 70 75 80 85 90 95 100  SEVERE iii. Enthesis Pain
       ○ Left plantar fascia   ○ Left Achilles tendon     ○ Right plantar fascia   ○ Right Achilles tendon iv. Dactylitis ("Sausage digit") ○ Current v. Spine  ○ Inflammatory back pain (SI and/or spine)  ○ SI X-ray changes  ○ Non-SI X-ray changes

FROM FIG. 6A

M. LABORATORY FINDINGS (Complete at each visit.)
i. Laboratory Findings (+/- 21 days of today's visit)
☐ None or Date of results ☐☐/☐☐/☐☐ (MM/DD/YY)

ESR _____ (West.)
CRP _____
CRP _____ (Upper Limit Normal)
WBC _____
Neutrophils _____ %
Hct _____ %

Plat's _____
Creat. _____
Alb. _____
AST _____ (SGOT)
ALT _____ (SGPT)
Hgb _____

Skin Testing (most recent or ever)
PPD: ○ +ve  ○ -ve
PPD Date: (MM/YY) ☐☐/☐☐/☐☐
If positive, was treatment prescribed?
○ No  ○ Yes ii. Laboratory Findings (most recent or ever)
CCP Abs _____ (ever)
CCP Abs _____ (Upper Limit Normal)
Date of results: (MM/DD/YY) ☐☐/☐☐/☐☐

RF _____ (ever)
RF _____ (Upper Limit Normal)
Date of results: (MM/DD/YY) ☐☐/☐☐/☐☐ iii. Laboratory Findings (most recent or ever)
☐ On lipid lowering Rx at the time of testing.
Date of results: (MM/DD/YY) ☐☐/☐☐/☐☐
Total Cholesterol (fasting) _____
HDL _____  LDL _____  Triglycerides _____

Chest X-Ray (most recent or ever) Date of results: (MM/DD/YY)
CXR results: ○ Normal  ○ Abnormal ☐☐/☐☐/☐☐

Site ID ☐
Copyright 2000-2008 © CORRONA, Inc.
2007-10-15 MD Bsl. v.7 Pg. 4 of 4
Page 4

UW Health Rheumatology Arthritis Program
CORRONA Physician Review Form

Page 1                                                                                     Site ID [    ]

Please complete this "ID info" and copy it onto EVERY PAGE of the questionnaire.

Patient ID [   ]-[  ]-[    ]         Date of office visit (MM/DD/YY) [  ]/[  ]/[  ]

Part I: COMPLETE AT EACH VISIT

A. Your CORRONA Physician ID number [    ] (2-digit)  ☐ Enrollment visit  ☐ Follow-up visit B. CURRENT RHEUMATIC DIAGNOSIS(ES). Fill all boxes and circles that apply. ("OP" = Osteoporosis)

Year of onset*  | Disease severity (fill one per Dx) 1=Mild → 5=Severe

☐ OA → [  ] → ○1 ○2 ○3 ○4 ○5    OA → PATIENTS WITH OA: JOINTS AFFECTED
                                        ☐ Hip  ☐ Knee  ☐ Spine  ☐ Hand  ☐ Other
☐ OP → [  ] → ○1 ○2 ○3 ○4 ○5

☐ OP risk → [  ] → ○1 ○2 ○3 ○4 ○5    PATIENTS WITH RA, JRA or PA
                                      Complete at each visit.
☐ New onset joint symptoms → Weeks since onset of signs or symptoms [  ]
                                      i. ARA Functional Class  ○I.  ○II.  ○III.  ○IV.

☐ RA → [  ] → ○1 ○2 ○3 ○4 ○5  RA →   ii. 28-Joint Counts  [  ]  [  ]
                              JRA →                      Tender  Swollen
☐ JRA (adult or child) → [  ] → ○1 ○2 ○3 ○4 ○5        iii. Subcutaneous nodules  ○No  ○Yes
☐ Psoriatic Arthritis → [  ] → ○1 ○2 ○3 ○4 ○5  PA →   iv. Clinical joint deformity  ○No  ○Yes
                                                       (hands, wrists, feet)
  → Indicate Subtype:  ☐ RA Like  ☐ Asymm. Oligo.      Complete box if blood has been obtained
                        ☐ Spondylitis  ☐ DIP            for genetic testing at this visit: ☐
  Psoriasis  | 1=Mild → 5=Severe                       Does patient now/ever meet ACR criteria for the
  → skin activity → ○1 ○2 ○3 ○4 ○5                     diagnosis indicated?   ○No  ○Yes

*Indicate at baseline OR IF NEW DX

C. PHYSICIAN GLOBAL ASSESSMENT OF CURRENT DISEASE ACTIVITY (refers to primary diagnosis)
Put a mark (like this | ) on the scale:

NOT ACTIVE ———————————————————————— VERY ACTIVE
0                                                    100

FROM FIG. 7A

"DISPATCHER" BOX

If follow-up: Since the last form, has the patient had:
If baseline: Has the patient ever had:

FILL ONE CIRCLE FOR EACH LETTER:    No   Yes   if "yes"   Complete corresponding section(s) on pp. 2-3.

| | | No | Yes | |
|---|---|---|---|---|
| D. | Hospitalization | → ○ | ○ → | D. on p.2 |
| E. | Infections | → ○ | ○ → | E. " " |
| F. | Comorbidities, Drug Toxicities, Fractures | → ○ | ○ → | F. " " |
| G. | Joint Surgery | → ○ | ○ → | G. " " |
| H. | Joint Arthrocentesis | → ○ | ○ → | H. " " |
| I. | Radiographs, MRI | → ○ | ○ → | I. on p.3 |
| J. | Bone Densitometry | → ○ | ○ → | J. " " |
| K. | Rx Added or Discontinued | → ○ | ○ → | K. " " |

Lastly, please complete L & M on p.3 at ALL VISITS

Site ID [ ]    Copyright 2000-2006 © CORRONA, Inc.
2006-01-01   MD Pg. 1 of 3
v.6     (Alternate Page 1)

FIG. 7B

CORRONA Patient Enrollment Questionnaire

Page 1                                                                 Site ID [    ]

Please complete the Patient ID information on every page of the questionnaire.

Patient ID [ ][ ][ ] - [ ][ ] - [ ][ ][ ][ ]     Date of office visit (MM/DD/YY) [ ][ ] / [ ][ ] / [ ][ ]

This questionnaire asks for information that no blood tests, X-rays, or any source other than you can give.
Please answer each question, even if you feel it is not related to you at this time.
There are NO right or wrong answers so please answer exactly as you think or feel.

Who referred you to this clinic?   ○ Self   ○ Primary Care Physician   ○ OB/GYN
                                   ○ Rheumatologist   ○ ER/Urgent Care   ○ Friend   ○ Other 1. When you get up in the morning, do you feel stiff?
   ○ Yes   ○ No 2. If your answer to the question 1 was "Yes", how long does it take until you are as limber as you will be for the day?
   Enter the number of hours and/or minutes: [  ] hours   [  ] min.

3. Please fill either a "NO" or "YES" circle for each of the following conditions to indicate if you have EVER had it. Whenever you answer "YES", please fill in the ONE best answer about when it began.

|   |   | NO | YES Less than 1 year ago | YES 1-5 years ago | YES More than 5 years ago |
|---|---|---|---|---|---|
| a | High blood pressure (hypertension) | ○ | ○ | ○ | ○ |
| b | Heart attack | ○ | ○ | ○ | ○ |
| c | Angina | ○ | ○ | ○ | ○ |
| d | Other heart disease | ○ | ○ | ○ | ○ |
| e | Congestive heart failure | ○ | ○ | ○ | ○ |
| f | Stroke/Mini-stroke | ○ | ○ | ○ | ○ |
| g | Cancer (type_____) | ○ | ○ | ○ | ○ |
| h | Skin cancer (not melanoma) | ○ | ○ | ○ | ○ |
| i | Skin Cancer (melanoma) | ○ | ○ | ○ | ○ |
| j | Lymphoma | ○ | ○ | ○ | ○ |
| k | Lung cancer | ○ | ○ | ○ | ○ |
| l | Breast Cancer | ○ | ○ | ○ | ○ |

FROM FIG. 8A

| | | | | | |
|---|---|---|---|---|---|
| m | Bronchitis or emphysema | ○ | ○ | ○ | ○ |
| n | Anemia (low red blood count) | ○ | ○ | ○ | ○ |
| o | Other blood problem | ○ | ○ | ○ | ○ |
| p | Stomach or duodenal (peptic) ulcer | ○ | ○ | ○ | ○ |
| q | Gastroesophageal reflux (GERD) | ○ | ○ | ○ | ○ |
| r | Gastrointestinal bleed (GI bleed) | ○ | ○ | ○ | ○ |
| s | Thyroid problem | ○ | ○ | ○ | ○ |
| t | Diabetes (sugar) | ○ | ○ | ○ | ○ |
| u | Psoriasis | ○ | ○ | ○ | ○ |
| v | Back or spine problems | ○ | ○ | ○ | ○ |
| w | Osteoporosis | ○ | ○ | ○ | ○ |
| x | Broken bones after age 50 | ○ | ○ | ○ | ○ |
| y | Cataracts | ○ | ○ | ○ | ○ |
| z | Depression | ○ | ○ | ○ | ○ |
| aa | Alcoholism | ○ | ○ | ○ | ○ |
| bb | Severe allergies | ○ | ○ | ○ | ○ |
| cc | Liver disease | ○ | ○ | ○ | ○ |

Site ID

Copyright 2000-2008 © CORRONA, Inc.
2007-10-15 Bsl. v.7 Pg. 1 of 4

Please turn to next page.

FIG. 8B

CORRONA Patient Enrollment Questionnaire

Page 2                                                                                    Site ID [    ]

Please complete the Patient ID information on every page of the questionnaire.

Patient ID [ ][ ][ ] - [ ][ ] - [ ][ ][ ][ ]     Date of office visit (MM/DD/YY) [ ][ ] / [ ][ ] / [ ][ ]

4. Have you had any of the following surgeries? Please fill all boxes that apply.

A. Replacement (arthroplasty) of:
   - ☐ Left Knee          ☐ Right Knee
   - ☐ Left Hip           ☐ Right Hip
   - ☐ Left Knuckles      ☐ Right Knuckles
   - ☐ Left Shoulder      ☐ Right Shoulder B. Other surgeries:
   - ☐ Open Heart         ☐ Chest (not open heart)
   - ☐ Abdomen            ☐ Hysterectomy
   - ☐ Prostate           ☐ Breast
   - ☐ Angioplasty or Stent C. Check here ☐ if you haven't had ANY of the surgeries listed above.

5. Have you ever been hospitalized for any of the following? Please fill all boxes that apply.
   ☐ Surgery  ☐ Heart  ☐ Ulcer  ☐ Pneumonia  ☐ Other infection  ☐ Other reason  ☐ No hospitalizations

NOTE: If your family history is completely unknown to you, please fill this box ☐ and go to question 8 on the next page.

6. On each row below, please read the disease and then fill the boxes under any family members who have had it.

| Family history | Father | Mother | Brother(s) | Sister(s) |
|---|---|---|---|---|
| a. Heart Disease/Heart Attack (MI) | ☐ | ☐ | ☐ | ☐ |
| b. Cancer of colon or rectum | ☐ | ☐ | ☐ | ☐ |
| c. Any other cancer | ☐ | ☐ | ☐ | ☐ |
| d. Diabetes Mellitus | ☐ | ☐ | ☐ | ☐ |
| e. Stroke | ☐ | ☐ | ☐ | ☐ |
| f. Alzheimer's Disease | ☐ | ☐ | ☐ | ☐ |
| g. Fracture of hip, spine or wrist AFTER age 50 | ☐ | ☐ | ☐ | ☐ |

FROM FIG. 9A

| 7. On each row below, please read the disease and then fill the boxes under any family members who have had it. | | | | | | | |
|---|---|---|---|---|---|---|---|
| Family history | Father | Mother | Brother(s) | Sister(s) | Child | Aunt | Uncle |
| a. Rheumatoid arthritis | ☐ | ☐ | ☐ | ☐ | ☐ | ☐ | ☐ |
| b. Osteoarthritis or degenerative arthritis | ☐ | ☐ | ☐ | ☐ | ☐ | ☐ | ☐ |
| c. Lupus (SLE) | ☐ | ☐ | ☐ | ☐ | ☐ | ☐ | ☐ |
| d. Osteoporosis | ☐ | ☐ | ☐ | ☐ | ☐ | ☐ | ☐ |
| e. Psoriatic arthritis | ☐ | ☐ | ☐ | ☐ | ☐ | ☐ | ☐ |
| f. Psoriasis | ☐ | ☐ | ☐ | ☐ | ☐ | ☐ | ☐ |

Site ID ☐

Copyright 2000-2008 © CORRONA, Inc.
2007-10-15 Bsl. v.7 Pg. 2 of 4

Please turn to next page.

FIG. 9B

CORRONA Patient Enrollment Questionnaire

Page 3                                                                    Site ID [      ]

Please complete the Patient ID information on every page of the questionnaire.

Patient ID [ ][ ][ ] - [ ][ ] - [ ][ ][ ][ ]     Date of office visit (MM/DD/YY) [ ][ ] / [ ][ ] / [ ][ ]

---

8. Fill in each box for any medical condition you have had.

| | | |
|---|---|---|
| ☐ Unusual fatigue | ☐ Heart pounding (palpitations) | ☐ Numbness or tingling of arms or legs |
| ☐ Loss of appetite | ☐ Swelling of ankles (edema) | ☐ Depression (feeling blue) |
| ☐ Skin rash or hives | ☐ Dark or bloody stools | ☐ Anxiety (feeling nervous) |
| ☐ Psoriasis | ☐ Dry eyes | ☐ Problems with thinking/confusion |
| ☐ Loss of hair | ☐ Sores in the mouth | ☐ Problems with memory/forgetfulness |
| ☐ Muscle pain, aches or cramps | ☐ Dry mouth | ☐ Problems with sleeping |
| ☐ Muscle weakness | ☐ Cough | ☐ Trouble swallowing |
| ☐ Pregnancy | ☐ Wheezing | ☐ Heartburn or stomach gas |
| ☐ Shortness of breath | ☐ Dizziness | ☐ Stomach pains or cramps |
| ☐ Pain in the chest | ☐ Back pain | |

Fill this box ☐ if you haven't had *ANY* of these medical conditions.

---

9. Indicate the drug(s) with which you are CURRENTLY being treated. Do not include drugs you are starting <u>after</u> this office visit.

i. ARTHRITIS MEDICATIONS / DMARDs

☐ I'm NOT taking any DMARDs

Oral medications: ☐ Arava *(leflunomide)*   ☐ Methotrexate (tablets or liquid)   ☐ *Other DMARD(s)*
  ☐ Azulfidine *(sulfasalazine)*   ☐ Minocin *(minocycline)*   ☐ Plaquenil *(hydroxychloroquine)*
  ☐ Imuran *(azathioprine)*   ☐ Neoral *(cyclosporine)*   ☐ I'm not sure

Injectable medications: ☐ Enbrel *(etanercept)*   ☐ Kineret *(lanakinra)*
  ☐ Humira *(adalimumab)*   ☐ Methotrexate (injection)

Infusion medications: ☐ Remicade *(infliximab)*        Date of last infusion [ ][ ] / [ ][ ] / [ ][ ]
  ☐ Orencia *(abatacept)*
  ☐ Rituxan *(rituximab)*        Did you receive IV steroids?   ○ No   ○ Yes

FROM FIG. 10A

| For patients using injectable medications or receiving infusions: | | |
|---|---|---|
| Did you experience redness, stinging, or a rash at the site of the injection? | ○ No | ○ Yes |
| Did you experience a painful or burning sensation with drug administration? | ○ No | ○ Yes |

For patients receiving intravenous infusions: Did you experience an infusion reaction?
(Chest tightness, change in blood pressure, rash, palpitations, breathing problems.)  ○ No  ○ Yes ii. NSAIDs

☐ I'm NOT taking any NSAIDs
☐ Aspirin (81 mg [Baby] or 325 mg)
☐ Celebrex *(celecoxib)*
☐ Ibuprofen (Motrin)
☐ Naproxen
☐ Other NSAID(s)
☐ I'm not sure iii. Osteoporosis drugs

☐ I'm NOT taking any osteoporosis drugs
☐ Actonel *(risedronate)*            ☐ Fosamax *(alendronate)*
☐ Aredia *(pamidronate)*             ☐ Miacalcin *(calcitonin)*
☐ Didronel *(etidronate)*            ☐ Boniva *(ibandronate)*
☐ Estrogen                           ☐ Reclast *(zoledronic acid)*
☐ Evista *(raloxifene)*              ☐ Other osteoporosis drug(s)
☐ Forteo *(teriparatide)*            ☐ I'm not sure Site ID [ ]   Copyright 2000-2008 © CORRONA, Inc.   Please turn to next page.
              2007-10-15 Bsl. v.7 Pg. 3 of 4

FIG. 10B

CORRONA Patient Enrollment Questionnaire

Page 4                                                                                          Site ID [    ]

Please complete the Patient ID information on every page of the questionnaire.

Patient ID [   ]-[  ]-[    ]    Date of office visit (MM/DD/YY) [  ]/[  ]/[  ]

---

9. Cont'd... OVER THE PAST 8 WEEKS have you taken any of the following drugs? Please fill all boxes that apply.

| GI Meds | Antidepressants | Analgesics |
|---|---|---|
| ☐ I'm not taking any of the following GI meds | ☐ I'm not taking any of the following antidepressants | ☐ I'm not taking any of the following analgesics |
| ☐ Prilosec *(omeprazole)* | ☐ Prozac *(fluoxetine)* | ☐ Tylenol *(acetaminophen)* |
| ☐ Prilosec OTC *(omeprazole)* | ☐ Zoloft *(sertraline)* | ☐ Advil, Nuprin *(ibuprofen)* |
| ☐ Prevacid *(lansoprazole)* | ☐ Paxil *(paroxetine)* | ☐ Alleve *(naproxen)* |
| ☐ Aciphex *(rabeprazole)* | ☐ Celexa *(citalopram)* | ☐ Ultram *(tramadol)* |
| ☐ Protonix *(pantoprazole)* | ☐ Effexor *(venlafaxine)* | ☐ Darvon *(propoxyphene)* |
| ☐ Nexium *(esomeprazole)* | ☐ Wellbutrin *(bupropion)* | ☐ Tylenol with codeine |
| ☐ Cytotec *(misoprostol)* | ☐ Elavil *(amitriptyline)* | ☐ Lortab, Vicodin *(hydrocodone)* |
|  | ☐ Lexapro *(excitalopram oxalate)* | ☐ Percocet *(oxycodone)* |
|  | ☐ Cymbalta *(duloxetine HCl)* | ☐ Pain patch |

OVER THE PAST 8 WEEKS have you taken a _Medrol-pac?_    ○ No    ○ Yes

OVER THE PAST 8 WEEKS have you taken any _Prednisone?_ (if yes, please indicate most recent dose.)

○ No　○ Yes → ○ 1 mg　○ 2-2.5 mg　○ 3-4 mg　○ 5-7 mg　○ 7.5-9 mg　○ 10 mg or more (daily)

---

10. What drugs have you taken in the past but DO NOT TAKE NOW?

| | | | |
|---|---|---|---|
| ☐ Actonel *(risedronate)* | ☐ Enbrel *(etanercept)* | ☐ Imuran *(azathioprine)* | ☐ Plaquenil *(hydroxychloroquine)* |
| ☐ Arava *(leflunomide)* | ☐ Estrogen | ☐ Kineret *(anakinra)* | ☐ Reclast *(zoledronic acid)* |
| ☐ Azulfidine *(sulfasalazine)* | ☐ Evista *(raloxifene)* | ☐ Methotrexate | ☐ Remicade *(infliximab)* |
| ☐ Boniva *(ibandronate)* | ☐ Forteo *(teriparatide)* | ☐ Miacalcin *(calcitronin)* | ☐ Ridaura *(auranofin)* |
| ☐ Cuprimine *(Penicillamine)* | ☐ Fosamax *(alendronate)* | ☐ Neoral *(cyclosporine)* | ☐ Rituxan *(rituximab)* |
| ☐ Didronel *(etidronate)* | ☐ Humira *(adalimumab)* | ☐ Orencia *(abatacept)* | ☐ Solganal *(gold)* |

---

11. Which of the following have you taken OVER THE PAST 8 WEEKS?

☐ Check here if you haven't taken ANY of these OVER THE LAST 8 WEEKS.

☐ Glucosamine → ○ 1500 mg    ○ 1000 mg daily or less

☐ Cholesterol lowering agent ( Lipitor, Lescol, Mevacor, Pravachol, Altocor, Crestor, Zocor, Vytorin)

☐ Chondroitin    ☐ Folic Acid    ☐ Fish Oil    ☐ Other non-prescription remedy or remedies ☐ Plavix    ☐ Evening Primrose Oil    ☐ Coumadin    ☐ Borage Seed Oil    ☐ Limbrel    ☐ Flax seed oil

FROM FIG. 11A

12. Do you exercise? ○ Not at all  ○ 1-2 times per week  ○ 3-4 times per week  ○ 5-6 times per week  ○ Daily
13. Do you smoke cigarettes?  ○ Not, never  ○ Yes, currently  ○ Yes, previously  ○ Yes, only socially
14. Do you drink alcoholic beverages?  ○ Not at all  ○ 1-3 per week  ○ 1-2 per day  ○ 3 or more daily  ○ On occasion
15. Do you take your medications as prescribed?
   ○ 0 - 25%  ○ 25 - 50%  ○ 50 - 75%  ○ 75-95%  ○ 95 - 100% of the time.

16. Your gender:  ○ Male  ○ Female    17. Your weight [  ] (lbs)   18. Your height [  ] (ft) [  ] (in)

19. Are you under 90 years old?  ○ No  ○ Yes → If "yes" your year of birth: [  ] (e.g. 1945)
20. Current work status:
   ↳ ○ Full time  ○ Part time  ○ Not working outside the home with pay  ○ Student  ○ Disabled  ○ Retired
21. Number of days lost from work over the past 3 months because of arthritis: ____.
22. Your living arrangement: ○ Spouse/partner  ○ Sibling  ○ Parents  ○ Sons/daughters  ○ Alone  ○ Sr. Residence
23. Your final year of education:
   ↳ ○ Primary  ○ High School  ○ College/University (Completed? ○ Yes  ○ No)  ○ Don't remember
24. Your marital status:  ○ Single  ○ Married  ○ Partnered  ○ Widowed  ○ Separated  ○ Divorced
25. Your ethnicity:  ○ Hispanic or Latino  ○ Non-Hispanic or Non-Latino
26. Your race (fill all that apply):  ○ White  ○ Black/African American  ○ Asian  ○ American Indian or Alaskan Native
   ○ Native Hawaiian or Pacific Islander  ○ Other Pacific Islander
27. Your insurance type:  ☐ Private  ☐ Medicare  ☐ Medicaid  ☐ No Insurance Site ID [  ]    Copyright 2000-2008 © CORRONA, Inc.
2007-10-15 Bsl. v.7 Pg. 4 of 4

FIG. 11B

CORRONA modified HEALTH ASSESSMENT (mHAQ) PATIENT QUESTIONNAIRE

PAGE 1 of 1
Patient ID: ___ - ___ - ___

Site ID _____
Date _____

Please mark the one response which best describes your usual abilities over the past few days:

| | Without ANY Difficulty | With SOME Difficulty | With MUCH Difficulty | UNABLE to do |
|---|---|---|---|---|
| 1.) Dress yourself, including tying shoelaces and doing buttons? | ___ | ___ | ___ | ___ |
| 2.) Get in and out of bed? | ___ | ___ | ___ | ___ |
| 3.) Lift a full cup or glass to your mouth? | ___ | ___ | ___ | ___ |
| 4.) Walk outdoors on flat ground? | ___ | ___ | ___ | ___ |
| 5.) Wash and dry your entire body? | ___ | ___ | ___ | ___ |
| 6.) Bend down and pick up clothing from the floor? | ___ | ___ | ___ | ___ |
| 7.) Turn regular faucets on and off? | ___ | ___ | ___ | ___ |
| 8.) Get in and out of the car? | ___ | ___ | ___ | ___ |

SUBJECT ASSESSMENT OF PAIN & DISEASE ACTIVITY

PAIN: How much pain have you had because of your arthritis since the last time you filled out this form? Put a mark on the scale (like this | ) to show how severe your pain has been.

NO PAIN  0 5 10 15 20 25 30 35 40 45 50 55 60 65 70 75 80 85 90 95 100  PAIN AS BAD AS IT COULD BE

DISEASE ACTIVITY: Considering all the ways arthritis affects you, put a mark on the scale (like this | ) to show how well you are doing.

VERY WELL  0 5 10 15 20 25 30 35 40 45 50 55 60 65 70 75 80 85 90 95 100  VERY POORLY

SKIN DISEASE ACTIVITY (Psoriasis Patients Only) Put a mark on the scale (like this | ) to show the activity of your SKIN DISEASE ONLY.

VERY ACTIVE  0 5 10 15 20 25 30 35 40 45 50 55 60 65 70 75 80 85 90 95 100  VERY POORLY

Copyright 2000-2008 © CORRONA, Inc.
2007-10-15 mHAQ v.7

UW Health Rheumatology Arthritis Program
**CORRONA modified HEALTH ASSESSMENT (mHAQ)
PATIENT QUESTIONNAIRE**

PAGE 1 of 1                              Site ID _____
Patient ID: ___ - ___ - ___              Date _____

Please mark the one response which best describes your usual abilities over the past few days:

|  | Without ANY Difficulty | With SOME Difficulty | With MUCH Difficulty | UNABLE to do |
|---|---|---|---|---|
| 1) Dress themselves, including tying shoelaces and doing buttons? | ___ | ___ | ___ | ___ |
| 2) Get in and out of bed? | ___ | ___ | ___ | ___ |
| 3) Lift a full cup or glass to their mouth? | ___ | ___ | ___ | ___ |
| 4) Walk outdoors on flat ground? | ___ | ___ | ___ | ___ |
| 5) Wash and dry their entire body? | ___ | ___ | ___ | ___ |
| 6) Bend down and pick up clothing from the floor? | ___ | ___ | ___ | ___ |
| 7) Turn regular faucets on and off? | ___ | ___ | ___ | ___ |
| 8) Get in and out of the car? | ___ | ___ | ___ | ___ |

SUBJECT ASSESSMENT OF PAIN & DISEASE ACTIVITY

PAIN

NO PAIN ———————————————— PAIN AS BAD AS
        0                              100   IT COULD BE

DISEASE ACTIVITY

VERY WELL ——————————————— VERY POORLY
        0                              100

SKIN DISEASE ACTIVITY (Psoriasis Patients Only)

VERY ACTIVE ——————————————— EXTREMELY ACTIVE
        0                              100

Copyright 2000-2006 © CORRONA, Inc.
i. mHAQ Pg. 1 of 1
v.6            (Alternate)

FIG. 13

CORRONA Physician Review Follow-Up

Page 1                                                                                          Site ID [ ]

Please complete the Patient ID information on every page of the questionnaire.

Patient ID [ ][ ][ ] - [ ][ ] - [ ][ ][ ][ ]     Date of office visit (MM/DD/YY) [ ][ ] / [ ][ ] / [ ][ ]

Always Complete at least Sections A, B, C, I, and M.  ☞ Flagged events require completing an Adverse Event Form.

A. Your CORRONA Physician ID number [ ] (2 digits) ☐ Check this box if form is being completed due to a NEW biologic start or biologic switch.

B. CURRENT RHEUMATIC DIAGNOSIS(ES). Please complete all boxes and circles that apply.

NEW DX Year of onset | Disease severity (fill one per Dx) 1=Mild → 5=Severe

- ☐ OA → [ ] → ○1 ○2 ○3 ○4 ○5  OA→ | PATIENTS WITH OA: JOINTS AFFECTED ☐ Hip ☐ Knee ☐ Spine ☐ Hand ☐ Other
- ☐ OP → [ ] → ○1 ○2→○3 ○4 ○5
- ☐ OP risk → [ ] → ○1 ○2 ○3 ○4 ○5

PATIENTS WITH NEW ONSET, RA, or PA  
Complete at each visit.
i. ACR Functional Class   ○I.  ○II.  ○III.  ○IV.

- ☐ New onset Undiff. Arth. (Not yet RA or PsA) → Weeks since onset of signs or symptoms [ ][ ]  New→ ii. 28-Joint Counts   [ ][ ] Tender   [ ][ ] Swollen

- ☐ RA → [ ] → ○1 ○2 ○3 ○4 ○5  RA→ iii. Subcutaneous nodules   ○No  ○Yes  ○New iv. Clinical joint deformity (hands, wrists, feet)   ○No  ○Yes  ○New

- ☐ Psoriatic Arthritis [ ] → ○1 ○2 ○3 ○4 ○5  PA→
  - → Indicate Subtype:  ☐ RA Like  ☐ Asymm. Oligo.  ☐ Spondylitis  ☐ DIP Complete box if blood has been obtained for genetic testing at this visit:  ☐ Biomarkers ☐

Is patient enrolled in CORRONA Psoriatic Pilot Study?  ○No  ○Yes

Does patient now/ever meet ACR criteria for the diagnosis indicated?   ○No  ○Yes

C. PHYSICIAN GLOBAL ASSESSMENT OF CURRENT DISEASE ACTIVITY (refers to primary diagnosis)

Put a mark (like this | ) on the scale:

NOT ACTIVE :..............................................: VERY ACTIVE
0 5 10 15 20 25 30 35 40 45 50 55 60 65 70 75 80 85 90 95 100

FROM FIG. 14A

| "DISPATCHER" BOX | Complete all corresponding sections IF patient has NEW incidence (Yes indicated below) since the last form was completed. |
|---|---|

FILL ONE CIRCLE FOR EACH LETTER:        No     Yes

D. Hospitalization → ○ ○
    E. Infections → ○ ○
    F. Comorbidities, Drug Toxicities, Fractures → ○ ○
    G. Joint Surgery → ○ ○
    H. Joint Arthrocentesis → ○ ○
    I. Concomitant Medications / Drug Switches → ○ ○
    J. Radiographs, MRI, Ultrasound → ○ ○
    K. Bone Densitometry → ○ ○

D. HOSPITALIZATION (new since the last form). Fill all boxes that apply.
☐ For RA, not related to joint arthroplasty, but for the disease process itself.
☐ For reasons other than RA disease process (specify):
    ☐ Drug-related toxicity (see sections E and F)   ☐ Joint anthroplasty   ☐ Unrelated medical problem Site ID [        ]     Copyright 2000-2008 © CORRONA, Inc.     Page 1
                       2007-10-15 MD FU v.7 Pg. 1 of 4

FIG. 14B

CORRONA Physician Follow-Up

Page 2                                                                                    Site ID [ ]

Please complete the Patient ID information on every page of the questionnaire.

Patient ID [ ][ ][ ] - [ ][ ] - [ ][ ][ ][ ]    Date of office visit (MM/DD/YY) [ ][ ] / [ ][ ] / [ ][ ]

E. INFECTIONS (new since last form). Fill all boxes that apply and indicate Pathogen.

| # - Infection Site: | MM/YY of onset | Path Code: | # - Infection Site: | MM/YY of onset | Path Code: |
|---|---|---|---|---|---|
| 1 - ☐ Joint/Bursa | / | | 8 - ☐ Other _____ | / | |
| 2 - ☐ Cellulitis | / | | 9 - ☐ Gastroenteritis | / | |
| 3 - ☐ Sinusitis | / | | ☐ UTI | | |
| 4 - ☐ Diverticulitis | / | | ☐ URI | | |
| 5 - ☐ Sepsis | / | | | | |
| 6 - ☐ Pneumonia | / | | | | |
| 7 - ☐ Bronchitis | | | | | |

Pathogen codes
CD = Coccidiodomycosis
CY = Cryptococcus
HA = H.zoster
HP = Histoplasmosis
LI = Listeria
NO = Non-opportunistic
OO = Other opportunistic
PN = Pneumocystis
TB = TB ☞ IF the patient was hospitalized, please enter the Infection Site(s) number listed above. [ ]
☞ IF the patient required IV antibiotics, please enter the Infection Site number listed above. [ ]
    IF the hospitalization was attributable to specific drug use, please enter the drug code. [ ] (Refer to Section F codes.)

F. COMORBIDITIES, DRUG TOXICITIES, FRACTURES (new since last form)
If any of the following are present, fill the box under "Co-M/Tox" and write the 2-digit month and year of onset.
If a drug toxicity, please select the most responsible drug code from the list below.

| Fill if Co-M/Tox | Drug Code | MM/YY of onset | Fill if Co-M/Tox | Drug Code | MM/YY of onset | Fill if Co-M/Tox | Drug Code | MM/YY of onset |
|---|---|---|---|---|---|---|---|---|
| ☐ Hypertension | | | ☐ Ulcer (peptic/bleeding) | | | ☐ Psychiatric disease (other) | | |
| ☐ CAD ☞ (Stent, CABG, Cath) | | | ☐ GERD | | | ☐ Depression | | |
| ☐ MI ☞ | | | ☐ Dyspepsia | | | ☐ Pulmonary fibrosis | | |
| ☐ CHF ☞ | | | ☐ Elevated creatinine | | | ☐ Asthma | | |
| ☐ Unstable Angina ☞ | | | ☐ Diarrhea | | | ☐ COPD | | |
| ☐ Edema | | | ☐ Nausea | | | ☐ Low WBC | | |
| ☐ Stroke/Mini-stroke ☞ | | | ☐ Liver disorder | | | ☐ Anemia | | |
| ☐ DVT | | | ☐ Drug-induced SLE | | | ☐ Diabetes mellitus | | |
| ☐ Lymphoma ☞ | | | ☐ Rash | | | ☐ Infusion reaction | | |
| ☐ Lung cancer ☞ | | | ☐ Psoriasis (not arthritis) | | | ○ Mild  ○ Moderate  ○ Severe | | |
| ☐ Breast cancer ☞ | | | ☐ Alopecia | | | ☐ Other _____ | | |
| ☐ Cancer (skin) ☞ | | | ☐ Demyelinating illness | | | ☐ Alcohol abuse  ○ Now  ○ Ever | | |
| ☐ Cancer (other) ☞ ↳ _____ | | | | | | ☐ IV drug use  ○ Now  ○ Ever | | |
| | | | | | | ☐ Tobacco use  ○ Now  ○ Ever | | |

FROM FIG. 15A

| Flagged events require completing an Adverse Event Form. (Additional payment offered.) |
|---|
| Were any of these toxicities reported to the FDA? ○ No ○ Yes  If Yes, enter drug code: ___ |

| DRUG CODES TO ENTER IN SECTIONS E and F: | | 21 Actonel | 29 Fosamax | 35 Celebrex |
|---|---|---|---|---|
| 51 Prednisone | 60 Kineret | 15 Remicade | 22 Aredia | 32 Invest. OP Drug | 40 Ibuprofen |
| 52 Arava | 10 MTX | 18 Rituxan | 24 Boniva | 31 Other OP Drug | 50 Invest. NSAID |
| 56 Enbrel | 17 Orencia | 20 Invest. DMARD | 23 Didronel | 33 Reclast | 41 Naproxen |
| 58 Humira | 99 Other drug | 19 Other DMARD | 28 Forteo | | 39 Other NSAID |

| Indicate the 2 most recent fractures (new since the last form). Enter month and year. |
|---|
| Most recent:  □ Wrist □ Hip □ Spine □ Rib(s) □ Pelvis □ Other   Yr. and |
| Second most recent: □ Wrist □ Hip □ Spine □ Rib(s) □ Pelvis □ Other   Mo. |

| G.  JOINT SURGERY (new since the last form.) Fill all boxes that apply. |
|---|
| Site: □ Hip    □ Knee    □ Hand/wrist □ Carpal tunnel □ Shoulder    Yr. and Mo. of |
|       □ Elbow  □ Foot/ankle □ C Spine  □ Other                       most recent |

| G.  JOINT ARTHROCENTESIS (new since the last form.) Include all steroid injections into joints, tendons, and bursa. |
|---|
| Do not include diagnostic aspirations.                    How many steroid injections? |
| Fill all that apply:□ Synvisc □ Hyalgan □ Supartz □ Orthovisc □ Eufflexa □ Corticosteroid  ○1  ○2  ○3  ○4+ |

Site ID       Copyright 2000-2008 © CORRONA, Inc.       Page 2
              2007-10-15 MD FU v.7 Pg. 2 of 4

FIG. 15B

CORRONA Physician Review Follow-Up

Page 3                                                                 Site ID [ ]

Please complete the Patient ID information on every page of the questionnaire.

Patient ID [ ][ ][ ] - [ ][ ] - [ ][ ][ ][ ]     Date of office visit (MM/DD/YY) [ ][ ] / [ ][ ] / [ ][ ]

i. CURRENT BIOLOGICS (Dose and Frequency)

| | |
|---|---|
| ○ Enbrel | ○ 25 mg once weekly  ○ 25 mg twice weekly  ○ 50 mg once weekly  ○ Other ____ |
| ○ Humira | ○ 40 mg every 2 weekly  ○ 40 mg weekly  ○ Other ____ |
| ○ Remicade | ○ Every 8 weeks  ○ Every 4 weeks  ○ Every 6 weeks  ○ Every ___ weeks  No. of vials: ___ |
| ○ Orencia | ○ First Dose  ○ 2 weeks after first dose  ○ 2 weeks after second dose |
| | ○ Every 4 weeks  ○ 2 vials = 500 mg  ○ 3 vials = 750 mg  ○ 4 vials = 1 g |
| ○ Rituxan | Date of last infusion ___ / ___ / ___    ○ 500 mg  ○ 1,000 mg  ○ Other ____ |
| ○ Kineret | ○ 100 mg daily   ○ Other ____ |
| ○ Other Biologic | |

CURRENT DRUGS (Please include any changes made today or since completing the last form.)

Drugs starting today or since last form = △
Drugs continued today or since last form = ○
Drugs discontinued today or since last form = □

□ Patient is not taking any of these drugs.

| | Dose (mg) | If Changed Today | Reason Code(s)* | Date of Start or Stop (MM) / (YY) |
|---|---|---|---|---|
| △ ○ □ Prednisone / d | | ○ | | / |
| △ ○ □ Arava / d | | ○ | | / |
| △ ○ □ Azulfidine / d | | ○ | | / |
| △ ○ □ Enbrel → | | ○ | | / |
| △ ○ □ Humira → | | ○ | | / |
| △ ○ □ Imuran / d | | ○ | | / |
| △ ○ □ Kineret → | | ○ | | / |
| △ ○ □ MTX / wk | | ○ | | / |
| △ ○ □ Orencia → | | ○ | | / |
| △ ○ □ Plaquenil / d | | ○ | | / |

(DMARD)

\* Reason Codes
If initiating or discontinuing therapy.

A - Lack of efficacy
B - Toxicity *
C - No longer needed
D - Lymphoma/malignancy
F - Formulary restriction

FROM FIG. 16A

| | | | | | | |
|---|---|---|---|---|---|---|
| H - Patient preference | △ ○ □ Remicade | → | ○ | | | |
| I - Control of disease | △ ○ □ Rituxan | → | ○ | | | |
| J - Infection | △ ○ □ Other Biologic | | ○ | | | |
| K - Lack of insurance | △ ○ □ Other DMARD | | ○ | | | |
| M - Recent journal report | △ ○ □ Invest. DMARD | → | ○ | | | |
| S - Recent meeting report | | | | | | |
| V - Recent lecture | △ ○ □ Actonel / wk | | ○ | | | |
| W - Withdrawn by FDA/Mfgr | △ ○ □ Aredia / 3 mo | | ○ | | | |
| X - Physician preference | △ ○ □ Boniva / mo | | ○ | | | |
| Z - Peer suggestion | ↳ □ IV □ PO | | | | | |

OP Drug:
- △ ○ □ Didronel / d
- △ ○ □ ERT/HRT / d
- △ ○ □ Evista / d
- △ ○ □ Forteo / d
- △ ○ □ Fosamax /wk
- △ ○ □ Miacalcin / d
- △ ○ □ Reclast / yr
- △ ○ □ Invest. OP Drug →
- △ ○ □ Other OP Drug

* If reason is toxicity, please enter specific toxicity and responsible drug code in Section F.

Site ID

Copyright 2000-2008 © CORRONA, Inc.
2007-10-15 MD FU. v.7 Pg. 3 of 4

Page 3

FIG. 16B

CORRONA Physician Review Follow-Up

Page 4   Site ID [ ]

Please complete the Patient ID information on every page of the questionnaire.

Patient ID [ ][ ][ ] - [ ][ ] - [ ][ ][ ][ ]   Date of office visit (MM/DD/YY) [ ][ ] / [ ][ ] / [ ][ ]

J. RADIOGRAPHS, MRI, ULTRASOUND (new since the last form.)

☐ MRI   ☐ Ultrasound
___ Erosions not seen on x-ray
___ Other bone changes
___ Active synovitis Date of *most recent* MRI, Ultrasound or Radiograph (MM/YY)
[ ][ ] / [ ][ ]

Radiographs - RA and PA Patients: (each finding requires a response)

|  | None | Old* | New | Old & New |
|---|---|---|---|---|
| Erosions | ○ | ○ | ○ | ○ |
| Joint space narrowing | ○ | ○ | ○ | ○ |
| Deformity | ○ | ○ | ○ | ○ |

☐ No previous for comparison *
☐ Healed erosion(s)

K. BONE DENSITOMETRY (new since the last form.)

Date of most recent BMD: (MM/YY) [ ][ ] / [ ][ ]

L spine ⁺○ [ ].[ ][ ] or ☐ Not available
        ⁻○
BMD (g/cm²) [ ].[ ]

Hip* ⁺○ [ ].[ ][ ] or ☐ Not available
     ⁻○
BMD (g/cm²) [ ].[ ]

Distal radius ⁺○ [ ].[ ][ ] or ☐ Not available
              ⁻○
BMD (g/cm²) [ ].[ ]

* "Hip" refers to: ○ Femoral Neck ○ Total Hip ○ Unknown

L. PSORIATIC ARTHRITIS i. CASPAR Criteria (Check all that apply.)
○ Current Psoriasis   ○ History of Psoriasis   ○ 1st/2nd degree relative with Psoriasis   ○ Typical nail changes
○ Negative RF   ○ Current Dactylitis   ○ Dactylitis in the past   ○ X-rays with juxta-articular new bone formation ii. Physician Global Assessment of Skin ........................................
   CLEAR 0 5 10 15 20 25 30 35 40 45 50 55 60 65 70 75 80 85 90 95 100 VERY SEVERE iii. Enthesis Pain
   ○ Left plantar fascia   ○ Left Achilles tendon   ○ Right plantar fascia   ○ Right Achilles tendon iv. Dactylitis ("Sausage digit") ○ Current v. Spine ○ Inflammatory back pain (SI and/or spine) ○ SI X-ray changes ○ Non-SI X-ray changes

FROM FIG. 17A

M. LABORATORY FINDINGS *(Complete at each visit.)*
i. Laboratory Findings (+/- 21 days of today's visit)

☐ None or  Date of results ☐☐/☐☐/☐☐
(MM/DD/YY)

| | | |
|---|---|---|
| ESR (West.) | Plat's | |
| CRP | Creat. | |
| CRP (Upper Limit Normal) | Alb. | |
| | AST (SGOT) | |
| WBC | ALT (SGPT) | |
| Neutrophils ___ % | Hgb | |
| Hct ___ % | | |

Skin Testing *(most recent)*    PPD Date: (MM/YY)
PPD: ○ +ve  ○ -ve                  ☐☐/☐☐
If positive, was treatment prescribed?
  ○ No  ○ Yes ii. Laboratory Findings *(most recent)*
CCP Abs _____   Date of results: (MM/DD/YY)
CCP Abs _____   ☐☐/☐☐/☐☐
  (Upper Limit Normal)

RF _____        Date of results: (MM/DD/YY)
RF _____        ☐☐/☐☐/☐☐
  (Upper Limit Normal)

ii. Laboratory Findings *(most recent)*
                  Date of results: (MM/DD/YY)
☐ On lipid lowering Rx at   ☐☐/☐☐/☐☐
  the time of testing.
Total Cholesterol (fasting) _____
HDL ___  LDL ___  Triglycerides ___

Chest X-Ray *(most recent)*  Date of results: (MM/DD/YY)
CXR results:                     ☐☐/☐☐/☐☐
  ○ Normal  ○ Abnormal Site ID ☐    Copyright 2000-2008 © CORRONA, Inc.    Page 4
             2007-10-15 MD FU v.7 Pg. 4 of 4

FIG. 17B

CORRONA Patient Follow-Up Questionnaire

Page 1                                                                                     Site ID [     ]

Please complete the Patient ID information on every page of the questionnaire.

Patient ID [   ] - [  ] - [    ]     Date of office visit (MM/DD/YY) [  ] / [  ] / [  ]

1. Fill in each box for any medical condition you have had *SINCE YOU LAST FILLED OUT THIS FORM.*

| | | |
|---|---|---|
| ☐ Heart attack | ☐ Unusual fatigue | ☐ Sores in the mouth |
| ☐ Angina | ☐ Loss of appetite | ☐ Dry mouth |
| ☐ Heart disease | ☐ Skin rash or hives | ☐ Cough |
| ☐ Congestive heart failure | ☐ Psoriasis | ☐ Wheezing |
| ☐ Stroke/Mini-stroke | ☐ Loss of hair | ☐ Dizziness |
| ☐ Skin cancer (not melanoma) | ☐ Muscle pain, aches or cramps | ☐ Back pain |
| ☐ Skin cancer (melanoma) | ☐ Muscle weakness | ☐ Numbness or tingling of arms or legs |
| ☐ Lymphoma | ☐ Pregnancy | ☐ Depression (feeling blue) |
| ☐ Lung cancer | ☐ Shortness of breath | ☐ Anxiety (feeling nervous) |
| ☐ Breast cancer | ☐ Pain in the chest | ☐ Problems with thinking/confusion |
| ☐ Other cancer (type) _____ | ☐ Heart pounding (palpitations) | ☐ Problems with memory/forgetfulness |
| ☐ Infection requiring hospitalization | ☐ Swelling of ankles (edema) | ☐ Problems with sleeping |
| ☐ Pneumonia requiring hospitalization | ☐ Constipation | ☐ Trouble swallowing |
| ☐ Fever | ☐ Diarrhea | ☐ Heartburn or stomach gas |
| ☐ Weight gain (>10 lbs) | ☐ Dark or bloody stools | ☐ Stomach pains or cramps |
| ☐ Weight loss (>10 lbs) | ☐ Dry eyes | ☐ Nausea |
| ☐ Headaches | ☐ Stuffy nose | ☐ Vomiting |

☐ Fill this box if you have not had ANY of these medical conditions *SINCE YOU LAST FILLED OUT THIS FORM*

2. Indicate the drug(s) with which you are CURRENTLY being treated. Do not include drugs you are starting <u>after</u> this office visit.

i. ARTHRITIS MEDICATIONS / DMARDs

☐ I'm NOT taking any DMARDs

Oral medications:  ☐ Arava *(leflunomide)*   ☐ Methotrexate (tablets or liquid)   ☐ Other DMARD(s)
   ☐ Azulfidine *(sulfasalazine)*   ☐ Minocin *(minocycline)*   ☐ Plaquenil *(hydroxychloroquine)*
   ☐ Imuran *(azathioprine)*   ☐ Neoral *(cyclosporine)*   ☐ I'm not sure

Injectable medications:   ☐ Enbrel *(etanercept)*   ☐ Kineret *(anakinra)*
   ☐ Humira *(adalimumab)*   ☐ Methotrexate (injection)

FROM FIG. 18A

| Infusion medications: | ☐ Remicade *(infliximab)*<br>☐ Orencia *(abatacept)*<br>☐ Rituxan *(rituximab)* | Date of last infusion ☐☐ / ☐☐ / ☐☐<br>Did you receive IV steroids?  ○ No  ○ Yes |
|---|---|---|

For patients using injectable medications or receiving infusions:
Did you experience redness, stinging, or a rash at the site of the injection?   ○ No  ○ Yes
Did you experience a painful or burning sensation with drug administration?   ○ No  ○ Yes

For patients receiving intravenous infusions: Did you experience an infusion reaction?
(Chest tightness, change in blood pressure, rash, palpitations, breathing problems.)   ○ No  ○ Yes

| ii. NSAIDs | ii. Osteoporosis drugs | |
|---|---|---|
| ☐ I'm NOT taking any NSAIDs<br>☐ Aspirin (81 mg [Baby] or 325 mg)<br>☐ Celebrex *(celecoxib)*<br>☐ Ibuprofen (Motrin)<br>☐ Naproxen<br>☐ Other NSAID(s)<br>☐ I'm not sure | ☐ I'm NOT taking any osteoporosis drugs<br>☐ Actonel *(risedronate)*<br>☐ Aredia *(pamidronate)*<br>☐ Didronel *(etidronate)*<br>☐ Estrogen<br>☐ Evista *(raloxifene)*<br>☐ Forteo *(teriparatide)* | ☐ Fosamax *(alendronate)*<br>☐ Miacalcin *(calcitonin)*<br>☐ Boniva *(ibandronate)*<br>☐ Reclast *(zoledronic acid)*<br>☐ Other osteoporosis drug(s)<br>☐ I'm not sure |

Site ID ☐

Copyright 2000-2008 © CORRONA, Inc.
2007-10-15 FU v.7 Pg. 1 of 2

Please turn to next page.

FIG. 18B

CORRONA Patient Follow-Up Questionnaire

Page 2                                                                 Site ID [    ]

Please complete the Patient ID information on every page of the questionnaire.

Patient ID [   ]-[  ]-[    ]     Date of office visit (MM/DD/YY) [  ]/[  ]/[  ]

2. Cont'd...
OVER THE PAST 8 WEEKS have you taken any of the following drugs? Please fill all boxes that apply.

| GI Meds | Antidepressants | Analgesics |
| --- | --- | --- |
| ☐ I'm not taking any of the following GI meds | ☐ I'm not taking any of the following antidepressants | ☐ I'm not taking any of the following analgesics |
| ☐ Prilosec *(omeprazole)* | ☐ Prozac *(fluoxetine)* | ☐ Tylenol *(acetaminophen)* |
| ☐ Prilosec OTC *(omeprazole)* | ☐ Zoloft *(sertraline)* | ☐ Advil, Nuprin *(ibuprofen)* |
| ☐ Prevacid *(lansoprazole)* | ☐ Paxil *(paroxetine)* | ☐ Alleve *(naproxen)* |
| ☐ Aciphex *(rabeprazole)* | ☐ Celexa *(citalopram)* | ☐ Ultram *(tramadol)* |
| ☐ Protonix *(pantoprazole)* | ☐ Effexor *(venlafaxine)* | ☐ Darvon *(propoxyphene)* |
| ☐ Nexium *(esomeprazole)* | ☐ Wellbutrin *(bupropion)* | ☐ Tylenol with codeine |
| ☐ Cytotec *(misoprostol)* | ☐ Elavil *(amitriptyline)* | ☐ Lortab, Vicodin *(hydrocodone)* |
|  | ☐ Lexapro *(excitalopram oxalate)* | ☐ Percocet *(oxycodone)* |
|  | ☐ Cymbalta *(duloxetine HCl)* | ☐ Pain patch |

OVER THE PAST 8 WEEKS have you taken a *Medrol-pac?*   ○ No   ○ Yes
OVER THE PAST 8 WEEKS have you taken any *Prednisone?* (if yes, please indicate most recent dose.)
    ○ No   ○ Yes → ○ 1 mg   ○ 2-2.5 mg   ○ 3-4 mg   ○ 5-7 mg   ○ 7.5-9 mg   ○ 10 mg or more (daily)

3. What drugs have you stopped taking since you last filled out this form?
☐ Actonel *(risedronate)*    ☐ Enbrel *(etanercept)*    ☐ Imuran *(azathioprine)*    ☐ Plaquenil *(hydroxychloroquine)*
☐ Arava *(leflunomide)*      ☐ Estrogen                 ☐ Kineret *(anakinra)*        ☐ Reclast *(zoledronic acid)*
☐ Azulfidine *(sulfasalazine)* ☐ Evista *(raloxifene)*  ☐ Methotrexate               ☐ Remicade *(infliximab)*
☐ Boniva *(ibandronate)*     ☐ Forteo *(teriparatide)*  ☐ Miacalcin *(calcitronin)*   ☐ Ridaura *(auranofin)*
☐ Cuprimine *(Penicillamine)* ☐ Fosamax *(alendronate)* ☐ Neoral *(cyclosporine)*     ☐ Rituxan *(rituximab)*
☐ Didronel *(etidronate)*    ☐ Humira *(adalimumab)*    ☐ Orencia *(abatacept)*       ☐ Solganal *(gold)*

4. Which of the following have you taken OVER THE PAST 8 WEEKS?
  ☐ Check here if you haven't taken ANY of these *OVER THE LAST 8 WEEKS.*
  ☐ Glucosamine → ○ 1500 mg   ○ 1000 mg daily or less
  ☐ Cholesterol lowering agent ( Lipitor, Lescol, Mevacor, Pravachol, Altocor, Crestor, Zocor, Vytorin)
  ☐ Chondrotin   ☐ Folic Acid   ☐ Fish Oil   ☐ Other non-prescription remedy or remedies
  ☐ Plavix   ☐ Evening Primrose Oil   ☐ Coumadin   ☐ Borage Seed Oil   ☐ Limbrel   ☐ Flax seed oil

FROM FIG. 19A

5. When you get up in the morning, do you feel stiff? ○ No ○ Yes
6. If your answer to question 5 was "yes", how long does it take until you are as limber as you will be for the day?
   Enter the number of hours and/or minutes: [  ] hours [  ] min.

7. Do you exercise? ○ Not at all ○ 1-2 times per week ○ 3-4 times per week ○ 5-6 times per week ○ Daily
8. Do you smoke cigarettes? ○ Not, never ○ Yes, currently ○ Yes, previously ○ Yes, only socially
9. Do you drink alcoholic beverages? ○ Not at all ○ 1-3 per week ○ 1-2 per day ○ 3 or more daily ○ On occasion
10. Do you take your medications as prescribed?
    ○ 0-25%  ○ 25-50%  ○ 50-75%  ○ 75-95%  ○ 95-100% of the time.

11. Your weight [   ] (lbs)     12. Your height [ ] (feet) [  ] (inches)

13. Current work status:
    ○ Full time  ○ Part time  ○ Not working outside the home with pay  ○ Student  ○ Disabled  ○ Retired
14. Number of days lost from work over the past 3 months because of arthritis: ____
15. Your living arrangement: ○ Spouse/partner ○ Sibling(s) ○ Parents ○ Sons/Daughters ○ Alone ○ Sr. Residence
16. Your marital status:  ○ Single  ○ Married  ○ Partnered  ○ Widowed  ○ Separated  ○ Divorced
17. Your insurance type:  ☐ Private  ☐ Medicare  ☐ Medicaid  ☐ No Insurance Site ID [        ]     Copyright 2000-2008 © CORRONA, Inc.
                       2007-10-15 FU v.7 Pg. 2 of 2

FIG. 19B

CORRONA Adverse Event (AE) Follow-Up Form
*Confirmation of Cancer/Malignancy*

Patient Identifier ___-___-___   Site ID: ____
Date of Event: mm ___ /dd ___ /yy ___ (Requires at least month and year)
Date of Report: ___ / ___ / ___

1. Can you confirm the event:☐ Confirmed  ☐ No such event occured.  ☐ This <u>same</u> event was reported in a previous visit.
   If confirmed, please identify how you confirmed the event:
   ☐ Reviewed source document(s) from hospital or other specialist (not your office notes).
   ☐ Patient reported history but no source documents available.
   ☐ Other (please explain) _____
   ☐ If no such event occured, please explain _____

2. Was the malignancy a lymphoma? ☐ Y  ☐ N  ☐ Unknown
   a) Was the lymphoma of  ☐ B cell origin  ☐ or T cell origin on biopsy?  ☐ Unknown
   b) Was the lymphoma a Hodgkin's lymphoma? ☐ Y  ☐ N  ☐ Unknown 3. Was the malignancy a skin cancer? ☐ Y  ☐ N  ☐ Unknown
   - If "Yes", was it a: ☐ basal cell carcinoma  ☐ squamous cell carcinoma  ☐ melanoma 4. What was the primary site/organ system of the cancer? _____ ( i.e. breast, lung, prostate, unknown)

5. Was a tissue diagnosis made (i.e biopsy)? ☐ Y  ☐ N  ☐ Unknown
   - What was the cancer type/histology (i.e. adenocarcinoma, small cell, etc.) _____

6. Was this the first cancer/malignancy in this patient?  ☐ Y  ☐ N  ☐ Unknown
   - If there was a prior cancer(s), what was (were) the organ system(s) previously involved? _____

7. Was this a recurrence of this specific malignancy (same site/organ system) in this patient? ☐ Y  ☐ N  ☐ Unknown 8. Was there spread to distant sites (organs other than lymph nodes) at the time of diagnosis? ☐ Y  ☐ N  ☐ Unknown 9. Is the patient deceased? ☐ Y  ☐ N  ☐ Unknown    * If deceased, please complete a CORRONA Exit Form 10. Did the investigator attribute the event to a specific drug? ☐ Y  ☐ N  ☐ Unknown
    - If yes, what was the drug name? _____

11. What is the office visit date that the patient was seen prior to this event? (mm ___ /dd ___ /yy ___)

12. Which biologics were used within the 6 months prior to the cancer/malignancy event?

a) Most recent TNF antagonist: Name _____ Dose _____ Frequency _____
                                   Date most recently infused/injected prior to the cancer/malignancy (mm/yy) ___/___
    b) Other biologic              Name _____ Dose _____ Frequency _____
                                   Date most recently infused/injected prior to the cancer/malignancy (mm/yy) ___/___
    c) ☐ No biologics were used in the previous 6 months.

Copyright 2000-2008 © CORRONA, Inc.
2008-01-17 C/M AE v.7

FIG. 20

CORRONA Adverse Event (AE) Follow-Up Form
*Confirmation of Infection*

Site ID: _____     Patient Identifier ___ - ___ - ___     Date of Report: ___/___/___
Type of Infection reported: _____     Pathogen reported: _____
Date of Infection: mm ___ /dd ___ /yy ___ (Requires at least month and year)
    OR:  ☐ No such event occurred.   ☐ This <u>same</u> infection was reported in a previous visit.

| 1. Was the infection diagnosed in the hospital <u>OR</u> did the infection require hospitalization? |  |
|---|---|
| ☐ YES | How was the information about the infection obtained? Check all that apply: <br> ☐ I took care of the patient during the hospitalization and had firsthand knowledge of the infection. <br> ☐ Review of hospital medical records (e.g. discharge summary) <br> ☐ Review of medical records from other physicians who took care of the patient in the hospital. <br> ☐ Patient self-reported the infection but no physician information was available. <br> ☐ Other (please explain) _____ |
| ☐ NO | How was the information about the infection obtained? Check all that apply: <br> ☐ I diagnosed the infection in my office and therefore had firsthand knowledge of the infection. <br> ☐ Review of medical records from other physicians ( e.g. office notes). <br> ☐ Patient self-reported the infection but no physician information was available. <br> ☐ Other (please explain) _____ |
| ☐ Unknown | |

1a. Did the patient receive prescription anti-infection medication(s) to treat the infection as an <u>*outpatient*</u> (e.g. antibiotics)?
    ☐ Y  ☐ N  ☐ Unknown 1b. Were any of these medications administered intravenously?
    ☐ Y  ☐ N  ☐ Unknown  ☐ Not Applicable 2. Is the type of the infection correctly indicated at the top of this page? ☐ Y  ☐ N  ☐ Unknown
    If no, what was the site (organ system)? _____

FROM FIG. 21A

3. Based upon culture or equivaltent methods (e.g. PCR), was a pathogenic organism identified? ☐ Y ☐ N ☐ Unknown
   If yes, what was the name of the organism (please be as specific as possible)? _____

4. Did you attribute the infection to a specific drug? ☐ Y ☐ N ☐ Unknown
   If yes, what was the drug name? _____

5. What is the office visit date that the patient was seen prior to this event? (mm ___ /dd ___ /yy ___)

6. Which biologics were used within the 6 months prior to the infection?
   a) Most recent TNF antagonist: Name _____ Dose _____ Frequency _____
      Date most recently infused/injected prior to the infection (mm/yy) ___/___
   b) Other biologic: Name _____ Dose _____ Frequency _____
      Date most recently infused/injected prior to the infection (mm/yy) ___/___
   c) ☐ No biologics were used in the previous 6 months.

7. Is the patient deceased? ☐ Y ☐ N ☐ Unknown
   If deceased, please complete a CORRONA Final Exit Form.

Copyright 2000-2008 © CORRONA, Inc.
2008-01-1 AE v.7

FIG. 21B

CORRONA Adverse Event (AE) Follow-Up Form
Confirmation of Cardiovascular Event
MI, Stroke, CHF or CAD

Patient Identifier ___ - ___ - ___     Site ID: _____
Date of Event: mm ___ /dd ___ /yy ___ (Requires at least month and year)    Date of Report: ___ / ___ / ___

1. Can you confirm the event: ☐ Confirmed  ☐ No such event occured.  ☐ This same event was reported in a previous visit.
   If confirmed, please identify how you confirmed the event:
   ☐ Reviewed source document(s) from hospital or other specialist (not your office notes).
   ☐ Patient reported history but no source documents available.
   ☐ Other (please explain) _____
   ☐ If no such event occured, please explain _____

2. If the event was a stroke, would it be most appropriately described as: (select one)
   ☐ Transient Ischemic Attack (TIA), i.e. mini-stroke less than 24 hours duration
   ☐ Ischemic stroke
   ☐ Hemmorhagic (bleeding) stroke 3. If the event was reported as a "cardiac" event, would it be most appropriately described as: (select one)
   ☐ Newly diagnosed coronary artery disease (based on stress test)
   ☐ Newly diagnosed coronary artery disease (based on cath/angiogram)
   ☐ Stable angina
   ☐ Unstable angina
   ☐ Angioplasty or stent procedure
   ☐ Myocardial infarction
   ☐ Bypass surgery procedure (CABG)
   ☐ New onset congestive heart failure (CHF) with reduced ejection fraction
   ☐ New onset congestive heart failure (CHF) with normal ejection fraction (diastolic dysfunction)
   ☐ Decompensation of prior congestive heart failure (CHF) with reduced ejection fraction
   ☐ Decompensation of prior congestive heart failure (CHF) with normal ejection fraction
   ☐ Other (please specify) _____

4. Is the patient deceased? ☐ Y ☐ N ☐ Unknown     * If deceased, please complete a CORRONA Exit Form 5. Did the investigator attribute the event to a specific drug? ☐ Y ☐ N ☐ Unknown
   * If yes, what was the drug name? _____

FROM FIG. 22A

6. Was the patient hospitalized? ☐ Y ☐ N ☐ Unknown

7. Did the patient have a prior history of any of the following: Please check all that are appropriate:
   ☐ coronary artery disease
   ☐ myocardial infarction
   ☐ stroke
   ☐ congestive heart failure
   ☐ no prior history of any of these events 8. What is the office visit date that the patient was seen prior to this event? (mm ___ /dd ___ /yy ___)

9. Which biologics were used within the 6 months prior to the cardiovascular event?
   a) Most recent TNF antagonist:  Name _____ Dose _____ Frequency _____
      Date most recently infused/injected prior to the cardiovascular event (mm/yy) ___/___
   b) Other biologic:              Name _____ Dose _____ Frequency _____
      Date most recently infused/injected prior to the cardiovascular event (mm/yy) ___/___
   c) ☐ No biologics were used in the previous 6 months.

Copyright 2000-2008 © CORRONA, Inc.
2008-01-17 CVD AE v.7

FIG. 22B

CORRONA DATA COLLECTION PROGRAM, Protocol 02-021
PARTICIPANT FINAL EXIT FORM Patient ID ___ ___ ___ - ___ ___ - ___ ___ ___             Site ID _____

Date of Discontinuation ___ / ___ / ___

Please mark the one response which best describes the reason for discontinuation of this patient:

☐ Patient withdrew consent

☐ Patient was Lost to Follow-up

☐ Death (Please provide date of death if known) ___ / ___ / ___

☐ Other _____

If death is indicated, please complete the following:

A) What was the diagnosis(es) of this patient?    ☐ RA  ☐ PsA  ☐ OA  ☐ OP
   ☐ OP risk   ☐ New Onset / Undiff Arth B) Please indicate cause of death below:
   a) ☐ Cardiovascular Disease (MI, CHF, arrhythmia)
   b) ☐ Clot (Pulmonary Embolus)
   c) ☐ Stroke / CVA
   d) ☐ Malignancy   ☐ Lymphoma   ☐ Solid Tumor    Type of tumor _____
   e) ☐ Infection   ☐ Sepsis   ☐ TB   ☐ Opportunistic    Name of organism _____
   f) ☐ Accident
   g) ☐ Other medical diagnosis    Medical diagnosis _____
   h) ☐ Unknown C) Was death related to a particular drug treatment?    ☐ Yes  ☐ No
   If yes, name of drug(s) _____

Copyright 2000-2008 © CORRONA, Inc.
2007-10-15 FE v.7 Pg. 1 of 1

FIG. 23

PARTICIPANT QUALIFICATIONS FORMS
Overview of Site/Physician Qualifications Please complete the following questions below:

1. What is the approximate patient population base served at your site? _____

2. Please estimate the total number of patients in the practice of each participating physician. _____

3. Please estimate the total number of patients served at your site who have been diagnosed with:

Rheumatoid Arthritis (RA) _____
   Osteoarthritis (OA) _____
   Psoriatic Arthritis (PsA) _____
   Osteoporosis (OP) _____
   Osteoporosis Risk (OP Risk) _____

4. Clinical coordinator(s):

Name: _____ Title: PA, NP, LPN, MA, Other _____
Years of research experience _____

Name: _____ Title: PA, NP, LPN, MA, Other _____
Years of research experience _____

Name: _____ Title: PA, NP, LPN, MA, Other _____
Years of research experience _____

Name: _____ Title: PA, NP, LPN, MA, Other _____
Years of research experience _____

Please direct any questions regarding this form to:
Kimberly Hinkle, MS, RN
Project Manager
Consortium of Rheumatology Researchers
 of North America, Inc.
Fonda, New York 12068
phone: (518) 853-1317
email: khinkle@frontiernet.net CONFIDENTIAL – This document contains proprietary information of CORRONA, and may not be used by the recipient for any purpose other

FIG. 24

Site/Physician Prior Research Experience

DMARD TRIALS (last 5 years)

Agent_____ Sponsor_____ Dates_____

Agent_____ Sponsor_____ Dates_____

Agent_____ Sponsor_____ Dates_____

Agent_____ Sponsor_____ Dates_____

Agent_____ Sponsor_____ Dates_____

Agent_____ Sponsor_____ Dates_____

Agent_____ Sponsor_____ Dates_____

Agent_____ Sponsor_____ Dates_____

Agent_____ Sponsor_____ Dates_____

Agent_____ Sponsor_____ Dates_____

- *In the event that you are precluded from disclosing the information requested above concerning DMARD trials due to confidentiality obligations, please provide the study dates and check off whether the study involved a biologic agent or a synthetic agent.*

Biologic Agent____ Synthetic Agent_____ Dates_____

Biologic Agent____ Synthetic Agent_____ Dates_____

Biologic Agent____ Synthetic Agent_____ Dates_____

Biologic Agent____ Synthetic Agent_____ Dates_____

OSTEOPOROSIS STUDIES (last 5 years)

Agent_____ Sponsor_____ Dates_____

Agent_____ Sponsor_____ Dates_____

Agent_____ Sponsor_____ Dates_____

---

CONFIDENTIAL – This document contains proprietary information of CORRONA, and may not be used by the recipient for any purpose other

FIG. 25

| | | |
|---|---|---|
| Agent_____ | Sponsor_____ | Dates_____ |
| Agent_____ | Sponsor_____ | Dates_____ |
| Agent_____ | Sponsor_____ | Dates_____ |
| Agent_____ | Sponsor_____ | Dates_____ |
| Agent_____ | Sponsor_____ | Dates_____ |
| Agent_____ | Sponsor_____ | Dates_____ |
| Agent_____ | Sponsor_____ | Dates_____ |

- In the event that you are precluded from disclosing the information requested above concerning osteoporosis studies due to confidentiality obligations, please provide the study dates and check off whether the study involved a biologic agent or a synthetic agent.

| | | |
|---|---|---|
| Biologic Agent____ | Synthetic Agent_____ | Dates_____ |
| Biologic Agent____ | Synthetic Agent_____ | Dates_____ |
| Biologic Agent____ | Synthetic Agent_____ | Dates_____ |
| Biologic Agent____ | Synthetic Agent_____ | Dates_____ |

Please direct any questions regarding this form to: Kimberly Hinkle, MS, RN
Project Manager
Consortium of Rheumatology Researchers
  of North America, Inc.
Fonda, New York 12068
phone: (518) 853-1317
email: khinkle@frontiernet.net CONFIDENTIAL – This document contains proprietary information of CORRONA, and may not be used by the recipient for any purpose other

FIG. 26

SYSTEM AND METHOD FOR COLLECTING AND MANAGING PATIENT DATA

CROSS-REFERENCE TO PRIOR APPLICATION

This application claims benefit from U.S. Provisional Application No. 61/085,095 filed Jul. 31, 2008, the entire content of which is incorporated herein by reference.

BACKGROUND OF THE INVENTION

1. Field of the Invention

The present invention relates to a system and method for collecting and managing patient data. More particularly, the present invention relates to a system and method that employs standardized data collection forms for use by health care providers and patients to enable efficient collection, storage and management of patient data for treatment of diseases, such as rheumatoid arthritis.

2. Description of the Related Art

Redesigning the delivery-of-care processes for diseases, such as rheumatic diseases within rheumatology practices and health systems, is critical to improving the outcomes and costs of care for patients. Traditional approaches to doing this work are generally inefficient, highly variable, and undependable. The complexity of the task is steadily increasing because of growing treatment options and expanding requirements for documenting services and disease outcomes. The electronic medical record actually does little to improve efficiency and physician functioning in and of itself; it merely stores whatever information we enter, in whatever format we enter it. A more fundamental redesigning of how we collect and manage information is needed, and the potential impacts of these efforts on outcomes and costs should be dramatic. Continuing with traditional approaches will lead to a further deterioration in outcomes, costs, and profits.

Accordingly, it is desirable to provide a system and method for efficiently collecting and managing patient data to assist in achieving improvements in patient treatment.

BRIEF DESCRIPTION OF THE DRAWINGS

These and other objects, advantages and novel features of the invention will be more readily appreciated from the following detailed description when read in conjunction with the accompanying drawings, in which:

FIGS. 2-26 are examples of forms and documents that can be used with the process shown in FIG. 1.

DETAILED DESCRIPTION OF THE EMBODIMENTS

Figure 1:
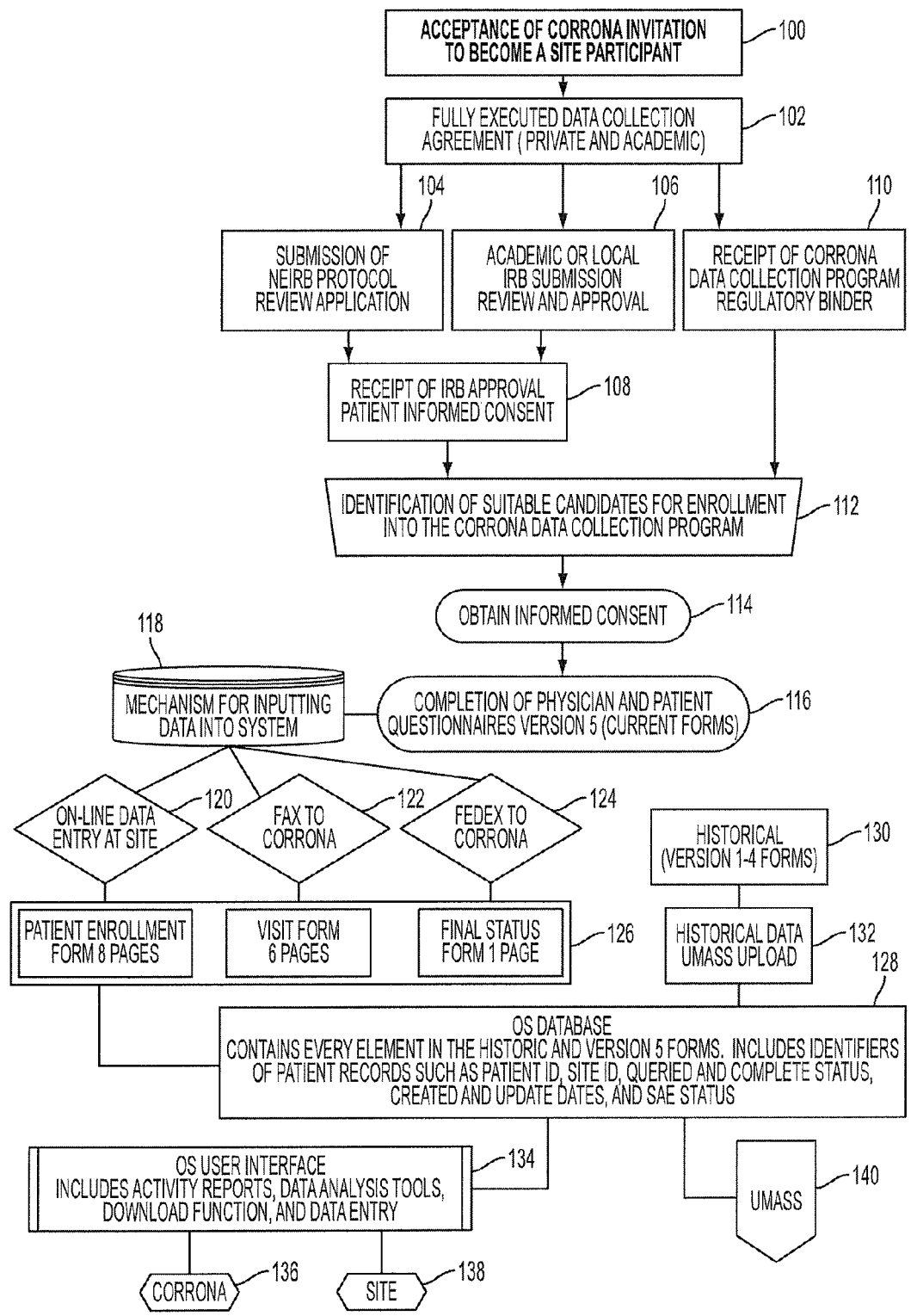
FIG. 1 is a flowchart illustrating an example of steps performed during a process for collecting and managing patient data according to an embodiment of the present invention.

The Consortium of Rheumatology Researchers of North America, Inc., or CORRONA, is a national organization assembled for the purpose of both gathering information and performing and facilitating clinical studies involving patients with rheumatic diseases, including rheumatoid arthritis (RA), psoriatic arthritis (PsA), osteoarthritis (OA), osteoporosis (OP), juvenile rheumatoid arthritis (JRA), and osteoporosis risk (OP Risk). CORRONA is built around principles that will revolutionize research concerning rheumatic diseases: gathering and organizing into a usable format comprehensive data about rheumatology patients that can be utilized to facilitate the clinical study process, improve patient care, and identify marketing trends. Through its expansive Data Collection Program, CORRONA will collect data about rheumatology patients from a mix of both academic and private practices from a geographic distribution reflecting our national character, with the potential to expand internationally. While others have collected information from patients alone for some time, CORRONA will collect data prospectively from both patients and physicians.

For instance, data on patients with RA will be collected, for example, every three months, while information on patients with PsA, OA, OP, and OP Risk will be collected, for example, every six months, using a set of forms and questionnaires designed to capture a wealth of data. The volume of subjects with the covered diagnoses will be very large; the database population is expected to reach more than 30,000. The process thus collects forms rich in clinical data from physicians and provides them with strong incentives, such as payment for completed forms and the provision of powerful customized computer applications developed by Clinforma designed to allow each site to access and manipulate data provided about the sites' own patients in new and exciting ways.

For example, sites will be able to generate graphic depictions of data for individual patients or patients grouped by diagnosis, physician, or practice-wide. This tool will give physicians the ability to analyze their practice data in a variety of creative and previously not possible ways which will make them both more efficient as care-givers and more attractive for future research funding. Sites will have the option of being additionally incentivized by participation in certain CORRONA revenue streams. The federal privacy rule-compliant authorization for release of information and research consent form explains to patients benefits associated with their participation as well.

The CORRONA Database can be used by, for example, two separate lines of business, referred to as the CORRONA Database Subscriptions and CORRONA Study Placement Services. Under the CORRONA Database Subscriptions line of business, CORRONA leases access to the prospectively collected data maintained in the CORRONA Database to pharmaceutical companies, contract research organizations (CROs), and other industry participants for purposes related to clinical, market, and outcomes research. These entities will not have direct access to the CORRONA Database. Rather, subscribers to the CORRONA Database will be able to pose questions to the CORRONA biostatistical support team, which will produce an appropriate report or other analytical document. Such research queries may target any aspect of the data collected (e.g., within the guidelines established by the CORRONA Board of Directors).

For example, subscribers may submit queries designed to compare characteristics of a particular agent with a group of generic drugs from the same treatment category (e.g., DMARDs or nonsteroidal anti-inflammatory drugs (NSAIDs)) or with a grouping of drugs with patent protection from these families. Generally, direct, head-to-head comparison of one proprietary agent against another will not be allowed. Work outputs from the CORRONA Database can be put to many uses. For example, information on actual clinical performance, toxicities, co-morbidities, hospitalizations, laboratory, radiographic and bone densitometry scores, along with sociodemographic data, can be used to create internal reports or prepare abstracts for presentation at scientific meetings. Manuscripts developed using these data will be attractive to scientific journals and other academic and more informal meetings of physicians. With this line of business, CORRONA will set a new standard in tracking drug performance.

Through the CORRONA Study Placement Services line of business, CORRONA will take much of the guesswork out of clinical trials, saving substantial time and money for those hoping to bring products to market, and ensuring that quality sites with eligible patients are given the opportunity to participate in clinical studies. The detailed patient information maintained in the CORRONA Database can be reliably matched against enrollment criteria for clinical studies to identify sites most capable of reaching enrollment targets. These detailed data profiles of patient characteristics will streamline the selection of sites for Phase II and III clinical investigations, in particular. The kind of information available through CORRONA will be invaluable for actually completing research investigations on schedule, saving significant time and money and getting products to patients more efficiently.

As will now be described in more detail, the embodiments of the present invention set forth herein provide a system and process for information gathering in real-time or substantially real-time. The system and method also provides a mechanism for the development of sophisticated reports suitable for abstract presentation and manuscript submission, and will significantly shorten the time needed to meet enrollment targets, saving considerable industry resources. In addition, participating sites will be given access to powerful tools that can revolutionize operations, and will enjoy the benefits associated with becoming industry's "first stop" for study placement.

As can be appreciated by health care providers, chronic disease management begins with having the necessary clinical information collected and organized in a way that promotes optimal therapeutic decision-making and, the monitoring of disease status and treatment safety. This activity accounts for a high percentage of a rheumatologist's work, most of it taking place during outpatient visits by established patients for rheumatoid arthritis (RA) and other chronic rheumatic diseases.

It thus can be beneficial to standardize data collection during the patient visit, to complete all possible aspects of data collection and organization before the physician-patient encounter, to provide real-time quantitative disease activity scoring, and to create a standardized physician dictation template based on this clinical data set. By performing these tasks, the rheumatologist-patient encounter can become more focused on analyzing and solving problems instead of collecting and organizing information.

At first, it is determined what information is needed to assess a patient's disease status and treatment safety risks, and to guide patient management. Patients self-report much of their history on the patient data form in the waiting room before entering the exam room. Further data collection by the physician in the examination room can also be structured in a series of 8 key questions on a form, and the results of the joint exam are recorded on a homunculus. Clinical and laboratory drug monitoring results are also reported. A standardized dictation template confirms the data collected on the forms, reports key findings, and lists other information necessary to the interpretation of the data and plans for treatment.

Further, to ensure efficiency and completeness in the data obtained for use in clinical trials, especially for biologic agents and other drugs, much of the biologic agent and other drug use is entered by the physician rather than relying on patient knowledge. The information regarding each biologic agent and other drug obtained from the editable forms includes dosage of each drug, the start and end dates for use of each drug, as well as a reason for any changes in dosage or use of any of the biologic agents or drugs. This information can be critical to both a clinical study as well as treatment for individual patients. For example, with the standardized listing of reasons for ending the use of a drug or biologic agent, a participating physician has an enhanced ability to prescribe treatments that would best fit the particular patient based on comparisons to similarly situated patients.

The data obtained through use of the standardized editable forms can also be expanded to further include the collection of additional laboratory elements to provide more information about cardiovascular (CV) disease. Additional laboratory elements may include lipid levels, high sensitivity CRP (hsCRP) waist circumference, body mass index, and blood pressure. Additionally, biomarkers can be collected to allow targeted whole genome scans.

In some embodiments, follow-up visits by the patient with the physician at regular intervals are mandated. By using the standardized editable forms at each of the mandated follow-up visits, comparative effectiveness can be examined, as well as an array of biomarkers, which may be associated with both response and toxicity. This combination of mandatory follow-up visits and use of standardized editable forms will provide more efficient clinical trials of biologics as well as a richer amount of information on each biologic for use by participating physicians to base treatment decisions.

Figure 2:
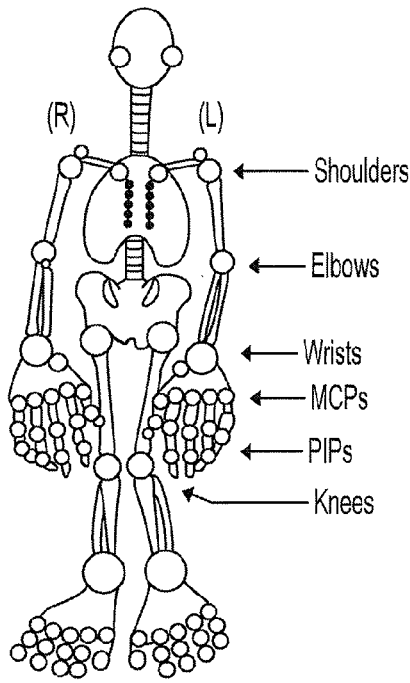
Figure 2:
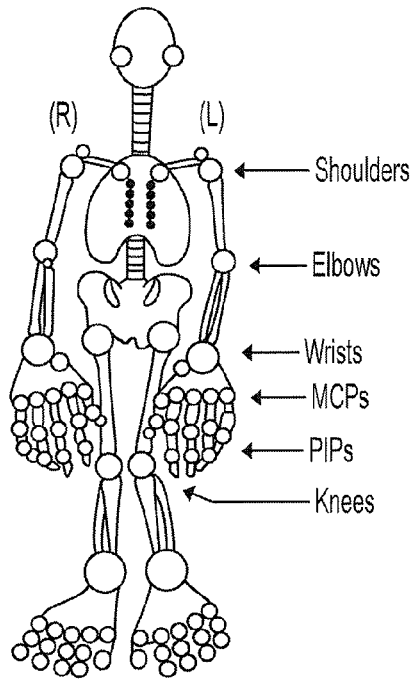

In addition, information is included on the forms for calculating a Global Arthritis Score (GAS) from the patient's visual analogue score (VAS) for pain, the mini-HAQ, and the tender joint count (see FIG. 2), including the tender joint homunculus. A physical exam checklist is also included in physician encounter forms. Furthermore, the separation of the patient-generated GAS components from the rheumatologist's global assessment of RA disease activity helps to distinguish active RA from other co-morbidities that may also contribute to pain, functional loss, and joint tenderness, such as accumulated joint damage, osteoarthritis, fibromyalgia, and non-rheumatic diseases, to name a few.

Also, patient-generated scoring systems can be used in clinical practice instead of the more complex and inclusive scoring systems used in clinical studies, such as the DAS28. Plotting disease activity and physician global scores from RA patients can separate those who require additional management and therapeutic acceleration from those needing other interventions, and those who could be managed by a mid-level provider or nurse monitoring visits. The CORRONA data forms also gather data relevant to psoriatic arthritis, osteoarthritis, osteoporosis, and ankylosing spondylitis, thus offering the prospect of standardizing data collection for established patients.

As will now be described more explicitly with regard to the flowchart shown in FIG. 1 and the forms shown in FIGS. 2-26, according to an exemplary embodiment of the present invention, the data collection process is basically a four step process: identifying and consenting patients, completing all patient and physician questionnaires, submission of the questionnaires, and putting a system in place to perform follow-up visits on patients enrolled in the database. An example of the benefits for the treating health care provider are substantial and include uniform documentation of level of service for billing, the ability to analyze all information submitted in an electronic interactive format, improved patient care, participation in future research studies, and substantial payment for submission of the forms to the database.

In step 100 of the flowchart shown in FIG. 1, a physician's office, for example, can be invited to become a site participant (e.g., the "site"). Upon accepting the invitation, personnel at the site, for example, can complete a data collection agreement in step 102, as well as participant qualification forms as shown in FIGS. 24-26. In doing so, the site can submit a New England Institutional Review Board (NEIRB) protocol review application in step 104, as well as an academic or local Institutional Review Board (IRB) review application in step 106. Upon receiving approval in step 108, the site can then begin to consenting patients for participation. Also, in step 110, the site can also receive the data collection program regulatory binder, which can include the forms as shown in FIGS. 2-26.

As show in step 112, the site can identify suitable candidates for enrollment in the program.

Identifying and Consenting Patients:

Once an eligible patient (e.g., a patient 17 years of age or older, and carrying a diagnosis of RA, PsA, OP, OA, OP risk, or JRA) has been identified by the principal investigator or sub-investigator, the patient is consented according to FDA guidelines in step 114. The patient is given adequate information (i.e., the patient informed consent ICF) and adequate time to discuss and have all questions answered in order to make an informed and voluntary decision about participating in the data collection program and/or sub-study. The patient will sign the ICF prior to any study related procedures, and a copy of the ICF is given to the patient. It is important to emphasize to the patient that the information collected is anonymous, that it is likely to improve patient care, and that it will be helping researchers from around the country better understand their disease and its outcomes.

A frequently employed script for consenting patient follows;

"We are asking your consent to collect information about your disease by having you complete a form. You do not have to participate in the process and if you choose not to, it will not affect the care you receive here. But, we hope that you do choose to participate as we believe that the process will improve patient care. Other doctors from around the country will be analyzing all of the data collected in order to help learn more about rheumatic diseases and osteoporosis. All of the data which is collected on you is completely anonymous. No one outside of this office will ever know the identity of the person completing the forms. No one will ever contact you because of your participation here, as no one will ever learn your identity. Your doctor is being paid for the forms. This payment is to reimburse them for the labor it takes to complete and gather the data. The physicians who oversee the data collection program will be leasing access to this information to the pharmaceutical industry. With the money earned, they wish to design and administer their own studies of drugs to treat rheumatic diseases. Your doctor will be able to create graphics and reports of your own laboratory values and clinical status. This can be used to track your progress on a particular drug or to monitor possible side effects. You will be able to access some of your own data via a password protected website."

The forms will typically take about 20 minutes of the patient's time initially, and than about 5-10 minutes, at the most, for follow-ups. In addition, patients are able to access elements of their own clinical status including joint counts, VAS and mHAQ scores directly over the Internet using their own password, which provides significant additional incentive to the patient to supply quality accurate information.

Completing Patient and Physician Questionnaires:

In step 116, patients with any of the diagnoses of RA, PsA, OP, OA, OP risk, or JRA complete, for example, a four page enrollment questionnaire and a one page mHAQ at the enrollment visit, examples of the forms being shown in FIGS. 8A-13. Randomization numbers are assigned manually as per the following algorithm: the first three numbers will be the site ID, the next two numbers are the MD ID, and the last four numbers are the patient ID, issued sequentially starting with 0001. The "site ID" in one example will be the first 3 numbers of any new ID manually generated. The next two numbers represent a specific physician or care provider within the practice, and the practice will keep a log of the key to these numbers. The last 4 digits of the code will be assigned sequentially in a log the practitioner keeps and will accommodate up to, for example, 9,999 patients at the practitioner's site.

On the forms, circles and boxes may be checked or filled, leading zeros are not required, and comments may be recorded in the margins of the forms as long as they do not obscure the data fields. The physician will complete, for example, a three page Physician Review Form (see FIGS. 3A-7B, for example) at the time of the enrollment visit. The portions of the questionnaires completed by the physician and patient will be held until lab results (ordered as part of routine care for this patient) are available and recorded on page 3 of the MD review form. At this time the forms may be submitted for inclusion into the database. When storing the completed forms, the forms can be kept separate from the chart, although they may be included in the chart if desired. A filing system where the forms are kept in numerical sequence allows for easy access to answer any queries related to the form submission, easy retrieval for billing documentation, and overall makes for a lighter load on the clinical chart and the staff handling these charts. Once a form is accepted into the database without queries, the information is easily accessed electronically via, for example, a computer, and any paper generated may be disposed of. However, the patient informed consent should be retained long-term, ideally in the patient clinic chart. In the event that a patient does not continue to participate in the data collection program, a Participant Final Exit Form can be completed and submitted along with any other forms from the practitioner's site.

Submission of Patient and Physician Questionnaires:

As shown in steps 118, 120, 122 and 124, in this example, forms may be submitted via one of three options: 1) Staff at the site may enter the data directly into an on-line form that is submitted via a secure Internet connection (step 120). 2) The site may forward the forms via facsimile to a location at which personnel manually enter the site's data (step 122); or 3) the forms can be sent via courier, such as Federal Express, to a location at which personnel manually enter the site's data (step 124). Naturally, there are pros and cons to each of the options, such as faster rate of reimbursement for on site data entry, elimination of queries to the site for on site data entry, consideration for personnel resources and time, etc.

As shown in FIGS. 3A-7B, the exemplary Physician Review Forms include spaces for entry of the following exemplary information: A 9 digit patient ID code; Date of office visit; Site ID number; Physician ID number (Box A); designation of enrollment or f/u visit (Box A); Diagnosis (Box B); Baseline diagnosis(es) must have a year of onset; On follow-up, if it is a new diagnosis for that patient, An onset date must be provided (Box B); Patients with RA, JRA or Psoriatic Arthritis must have a 28 joint count (Box B—See FIG. 2); A ratingtic mark for the 5 digit numerical scale for Disease Severity (Box B); A tic mark on the visual analogue scale of Current Disease Activity (Box C); Circle in the dispatcher box is complete as "yes" and the corresponding section on pages 2 or 3 is not completed; Pathogen is not indicated when an infection has been indicated. At least one box must be checked. (Box E); Year of onset of any of the elements in the "Comorbidity/Toxicity" section is completed without a year/month of onset (Box F); Radiographic section for RA. JRA, PA (Box I) is missing a response to either "erosions", "joint space narrowing" or "deformity" (Box I); If the Dexa is performed, numerical. T score results and or date must be present. Note: if there is a result for only the L spine, the hip, or the distal radius and not the other elements, the presence of one of the three is enough. Hip type must be complete (Box J); If a DMARD, NSAID, or Osteoporosis drug is changed, there must be a reason completed in the adjoining box. If the reason is toxicity, be sure to enter a drug code in Box F if applicable. At least one box must be selected in Box L, all drugs the patient is currently on, and those either newly prescribed or discontinued the day of visit are captured here; Date of the blood draw or "none" box must be checked in Box M. If lab section is dated, lab values must be entered. (Box M).

As further shown in FIGS. 8A-13, the exemplary patient review forms include spaces for entry of the following exemplary information: 9 digit patient ID; Date of office visit; Site ID number; Page 3, section 9, items i, ii, and iii: at least one box must be checked in each of the sections; Prednisone use must be indicated. Page 4, section 9; Questions 15, 16, 18, 19, 25, and 26 must be completed. As further shown, the exemplary patient follow-up forms include spaces for entry of the following exemplary information: 9 digit patient ID code; Date of office visit; Site ID number; Page 1, section 2, items i, ii, and iii, must have at least one box is checked in each of the sections i, ii, and iii; Prednisone use must be indicated. Page 2, Section 2; Questions 10, 12, and 16 must be completed.

The following are exemplary steps for completing the Physician forms:

Step 1. Enter physician id number (assigned by the staff person in charge of the data collection project) and indicate whether a baseline or follow-up visit.

Step 2. Fill in the Diagnosis (SES) box (es); if baseline or new onset, enter year of disease onset. Estimate year without going back to the chart.

Step 3. If RA, PsA, or JRA complete the 28 joint count. This is best done by moving down from the shoulders to the knees. Again, the joints covered in the 28 joint count are: shoulders, elbows, wrists, MCPs, PIPS and knees only. The 28 joint count homunculus is included as part of the protocol for your reference. Some insurance carriers will want the precise joints involved to be captured, for which the homunculus can be used. If OA, fill in the location. If osteoporosis or osteoporosis risk (anyone who is being treated with an antiresorptive agent who does not satisfy the strict criteria for osteoporosis), simply rate severity in the circles. A "risk severity" for osteoporosis may seem artificial. Estimate the risk to the patient of progression, given the circumstances of their overall health picture, meds etc. Place a mark on the 10 cm line indicating the disease activity today (an individual may have bad disease severity, but not much disease activity at the time of this evaluation). Rate activity of osteoporosis risk by judging the factors present which would impact on this outcome.

Step 4. Go to the Dispatcher Box. Any circle which is answered "no" will have a corresponding section in the next 2 pages which can be skipped. Any circle which is answered "yes", will have a corresponding section in the next 2 pages which must be completed. For the enrollment visit: Go directly to the top of p.2 (before completing the dispatcher box circles). I then ask, "Have you ever been in the hospital?" (baseline), or "Have you been hospitalized since the time of the last form?" (follow-up). Most adults have been in the hospital in their life. There is no need to take the time to hear about the gallbladder or appendectomy. Continue (after marking the box "unrelated medical problem") and ask, "Have you ever had pneumonia? Have you ever had a sinus infection or infection of the joints or skin?" Complete the appropriate answers. Remember to check the .non-opportunistic infection" box for URIs, UTIs, sinusitis, pneumonia etc. as appropriate and applicable. If you don't check this box, it will generate a query. Then move on the section F on P.2 which asks specifically about comorbidities or toxicities. A baseline exam requires you to ask all of the questions and determine if the recorded positive response was associated with a drug or not. Either way, the year of the event should again be estimated from the patient's description. (In 2004, if the pt states "about 10 yrs ago," record 1994 in the box without going back to the patient's chart to document the actual year. Complete the rest of this section. Any medically significant co-morbidity not listed here may be handwritten in the margins. The on-line version of the MD form has a comments section to capture this type of information. If there are no positives, continue.

Step 5. After completing the bottom of p.2 (self-explanatory), go to the top of p.3 . Fill in the characteristics of the joint xrays. Most baseline films will be completed under the "Old" designation for erosions etc. If an old film is available for comparison to a new film that shows new damage in any of the designated areas, record the changes under both "Old" and "New", as the case may be, but it is not necessary to go back through the old films at baseline because the database is interested in recording new information on the effects of drugs moving forward from the baseline. In the future, when repeat films are obtained, complete the New or Old designation and whether or not there is a "Healed erosion".

Step 6. Dexa scores. Designate whether your hip score represents a total hip or femoral neck and tell us which machine is being used.

Step 7. Section K, "Rx added or discontinued" is important. If any of the medications in these categories (DMARDs, NSAIDs, or antiresorptive agents) are being changed, give the reason. Do not record drug changes made before today on enrollment visits. On a follow-up visit, if a medication was discontinued since the last visit, but before this visit (by telephone direction, or by the pt themselves for whatever reason), this should be recorded in the appropriate box.

Step 8. "L" has to be completed at each visit.

Step 9. At this point, return to the bottom of p.1 and quickly complete the yes or no questions in the dispatcher box. For the follow-up visit: After the first half of page one of the physician review form is completed proceed directly to the Dispatcher box (this is in contrast to the sequence for completion of the forms at the Enrollment visit). Any circle which is answered "no" will have a corresponding section in the next 2 pages which can be skipped. Any circle which is answered "yes", will have a corresponding section in the next 2 pages which must be completed. If all answers are no, then the physician can proceed directly to page three and complete boxes L and M to complete his/her portion of the encounter.

Step 10. A staff member completes the lab section from the data which arrives back in the physicians' office on labs ordered and associated with this visit.

Step 11. Once the labs are entered, the forms are now ready to submit for data entry after final review. Questions can be considered during review such as: Are there years of onset for each diagnosis on the baseline visit? Missing joint counts? Missing info on presence or absence of deformities or nodules? Are there discrepancies between boxes which are checked on the first page "dispatcher box" and what is found (or not found) on the next 2 pages?

Step 12. The forms which have been submitted are now placed in a "submitted, but not confirmed as acceptable" file. They will remain there until your site receives the query summary from the data collection coordinator (if the site is forwarding the forms for personnel manual entry.) Once all queries have been answered, they can be placed in the chart (or otherwise) where they document the level of encounter for billing and monitoring purposes. The documentation is available electronically.

As shown in step 126, the enrollment forms can be gathered, and in step 128, the information on the forms can be entered into the database (the CORRONA database as discussed above). The historical version of the forms, and the historical data, can be stored and retrieved in steps 130 and 132. Also, in step 134, a user interface can be established so that a user can perform operations to, for example, generate activity reports, analyze the data using data analysis tools, download the data, and enter further data, to name a few. The users can be, for example, personnel at CORRONA as indicated in step 136, or personnel at the physician's site as indicated in step 138. Furthermore, as indicated in step 140, the information in the database can be uploaded in mass if desired.

Follow-Up Visits

Follow-up visits can be completed at the following frequency: RA patients—no more frequently than every three months, for example; all other diagnoses—no more frequently than every six months, for example. Follow-up visits can use a two page patient follow-up questionnaire as shown in FIGS. 18A-B and 19A-B, and the one-page mHAQ as shown in FIG. 12 or 13. At the time of the follow-up visit, the physician can complete, for example, the Physician Review Follow-up Form as shown in FIGS. 14A-17B, which can be the same or substantially the same as the Physician Review Form used at the baseline visit as shown in FIGS. 3A-6B only the order of completion is changed. A colored sticker or logo sticker may be placed on the outside cover of the patient's clinical chart which will make that patient more readily identifiable to physician, coordinator, and all other office staff as a participant.

Also, other diagnoses forms such as those shown in FIGS. 20-22B can be completed by the physician. Additionally, a history of the dates the patient has actually completed questionnaires, as well as the identifying number should be recorded inside the face page of the patient's clinical chart. This will allow staff to determine immediately at the time of any future appointments if a patient is due for a follow-up evaluation. Blank follow-up forms could be stockfiled in the exam rooms so that the health care provider can perform the follow-up evaluations independently. Alternatively, the individual performing the data entry could prepare charts and have the follow-up forms available at the time of check in for the patient to complete, while the physician form remains with the chart. If copies of MD/patient questionnaires are routinely stocked in exam rooms, the physician may proceed independently with the follow-up physician assessment without the assistance of auxiliary staff to complete the visit.

Although only a few exemplary embodiments of the present invention have been described in detail above, those skilled in the art will readily appreciate that many modifications are possible in the exemplary embodiments without materially departing from the novel teachings and advantages of this invention. For example, the order and functionality of the steps shown in the processes may be modified in some respects without departing from the spirit of the present invention. Accordingly, all such modifications are intended to be included within the scope of this invention.

The invention claimed is:

1. A method for collecting and managing patient data, the method comprising:
    collecting patient data by the following steps:
        generating sets of fillable forms using a computer for recording respective historical and clinical information regarding a respective medical condition affecting each of a plurality of authorized patients at a plurality of different unaffiliated participating sites, wherein each set of fillable forms for a plurality of authorized patients having the respective medical condition contains the same queries and answer keys to enable standardized answers to at least some of the queries from the authorized patients and participating physicians;
        each set of fillable forms is filled in by one of the plurality of authorized patients and that patient's participating physician using the following steps:
            presenting one portion of the set of editable forms to the authorized patient;
            the authorized patient fills in the first portion of the set of fillable forms;
            presenting another portion of the set of fillable forms to the authorized patient's participating physician; and
            the participating physician fills in the another portion of the set of editable forms, wherein information entered by the participating physician includes dosage and start and end dates for each biologic agent used by the authorized patient; and
    managing patient data by the following steps:
        generating a database using a computer comprising the information entered by authorized patients and participating physicians according to the patient data collecting step; and
        analyzing the information in the database to provide desired outputs for access by authorized users, wherein the information in the database is usable by authorized users for researching at least the respective medical condition, researching treatments for at least the respective medical condition, obtaining clinical evidence for the effectiveness and toxicity of drugs or treatments of at least the respective medical condition, selecting treatments for at least one of the authorized patients, evaluating treatments, or facilitating more informed patient management by the physician.

2. The method of claim 1, wherein access to information in the database is provided for at least one of the following purposes: researching at least the respective medical condition, researching treatments for at least the respective medical condition, obtaining clinical evidence for the effectiveness and toxicity of drugs or treatments of at least the respective medical condition, selecting treatments for at least one of the authorized patients, evaluating treatments, or facilitating more informed patient management by the physician.

3. The method of claim 1 further comprising providing incentives to participating physicians to participate, the incentives include at least one of payments for completed editable forms and access to the database.

4. The method of claim 1 further comprising providing access to analyses derived from the database to pharmaceutical companies or contract research organizations.

5. The method of claim 4, wherein the analyses include comparative effectiveness and toxicity of drugs or treatments.

6. The method of claim 1 further including the step of matching detailed patient information in the database to enrollment criteria for clinical studies to identify sites most capable of reaching enrollment targets.

7. The method of claim 1, wherein the respective medical condition is a rheumatic disease.

8. The method of claim 7, wherein the rheumatic disease is at least one of the following: rheumatoid arthritis (RA), psoriatic arthritis (PsA), osteoarthritis (OA), osteoporosis (OP), and osteoporosis risk (OP Risk).

9. The method of claim 1 further comprising the step of forming a quantitative disease activity score from the information provided in the editable forms.

10. The method of claim 1, wherein the type of information on the respective forms entered by the patient and physician includes the patient's visual analogue score (VAS) for pain, a health assessment questionnaire (HAQ), and a tender and swollen joint count.

11. The method of claim 10, wherein the tender joint count includes indications of tenderness and swollenness for twenty-eight joints.

12. The method of claim 1 further comprising adding information entered on said editable forms to the database by at least one of the following: on-line data entry, facsimile, mail, and courier.

13. The method of claim 1 further comprising providing access to said editable forms to each of the authorized patients and participating physicians at follow-up visits so as to add further information to the authorized patient's record.

14. The method of claim 1, wherein said information entered by the participating physician includes physician-supplied reasons for the authorized patient to end the use of any biologic agent.

15. The method of claim 1, wherein said information entered by the participating physician includes dosage and start and end dates for all anti-rheumatic drugs used by the authorized patient.

16. The method of claim 1 comprising the steps of transferring the information from the editable forms to a computer at the participating site and then transferring the information from the participating site via the internet to the database at a central location.

17. The method of claim 1, wherein the step of manipulating the information in the database to provide desired outputs for access by authorized users includes providing access to information in the database regarding an authorized patient to that authorized patient and their physician.

18. The method of claim 1, wherein the desired outputs include activity reports and data analysis tools.

19. The method of claim 1, wherein authorized users are provided access to analyses derived from the database, the access to analyses is provided by queries submitted by the authorized users.

20. The method of claim 19, wherein the queries submitted by the authorized users are evaluated, modified, or both to better accomplish intended goals of the authorized users.

21. The method of claim 19, wherein the authorized users are participating physicians using the information for creation of manuscripts and articles.

\* \* \* \* \*